United States Patent
Kummel et al.

(10) Patent No.: US 10,113,151 B2
(45) Date of Patent: Oct. 30, 2018

(54) COMPOSITION OF VIRAL VECTORS IN LECITHIN LIPOSOMES, PREPARATION METHOD AND TREATMENT METHODS

(71) Applicant: The Regents of the University of California, Oakland, CA (US)

(72) Inventors: Andrew C. Kummel, San Diego, CA (US); Sarah L. Blair, La Jolla, CA (US); Tony R. Reid, La Jolla, CA (US); William C. Trogler, Del Mar, CA (US); Farah Hedjran, La Jolla, CA (US); Natalie Mendez, Miramar, CA (US); Vanessa Herrera, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/439,095

(22) PCT Filed: Oct. 28, 2013

(86) PCT No.: PCT/US2013/067075
§ 371 (c)(1),
(2) Date: Apr. 28, 2015

(87) PCT Pub. No.: WO2014/070659
PCT Pub. Date: May 8, 2014

(65) Prior Publication Data
US 2015/0284691 A1    Oct. 8, 2015

Related U.S. Application Data

(60) Provisional application No. 61/719,574, filed on Oct. 29, 2012.

(51) Int. Cl.
*C12N 7/00*      (2006.01)
*A61K 9/127*    (2006.01)
(Continued)

(52) U.S. Cl.
CPC .............. *C12N 7/00* (2013.01); *A61K 9/1272* (2013.01); *A61K 39/0011* (2013.01);
(Continued)

(58) Field of Classification Search
None
See application file for complete search history.

(56) References Cited

U.S. PATENT DOCUMENTS 4,487,829 A * 12/1984 Sharp ................... C07K 16/081
                                                                435/339
2011/0229529 A1    9/2011 Irvine et al.

FOREIGN PATENT DOCUMENTS

WO        2001034130 A1    5/2001

OTHER PUBLICATIONS

Vorburger et al. Adenoviral Gene Therapy, The Oncologist, 2002;7:46-59.*
(Continued)

*Primary Examiner* — Michelle S Horning
(74) *Attorney, Agent, or Firm* — Greer, Burns & Crain, Ltd.; Steven P. Fallon

(57) ABSTRACT

A composition is provided which comprises a recombinant viral particle comprising a capsid, wherein the viral particle is encapsulated into an anionic liposome comprising lecithin and polyethylene glycol (PEG). A method for preparing and purifying the encapsulated viral particles is provided as well. Methods for treating patients by using the encapsulated viral particles are provided as well.

11 Claims, 21 Drawing Sheets

Specification includes a Sequence Listing.

(51) Int. Cl.
    A61K 39/00    (2006.01)
    A61K 39/12    (2006.01)
    A61K 48/00    (2006.01)
(52) U.S. Cl.
    CPC .......... *A61K 39/12* (2013.01); *A61K 48/0041*
        (2013.01); *A61K 2039/5258* (2013.01); *A61K
        2039/55555* (2013.01); *A61K 2039/6093*
        (2013.01); *C12N 2710/10032* (2013.01); *C12N
        2710/10034* (2013.01); *C12N 2710/10043*
        (2013.01); *C12N 2710/10051* (2013.01)

(56) References Cited

OTHER PUBLICATIONS

Immordino et al. Stealth liposomes: review of the basic science, rationale, and clinical applications, existing and potential. Int J Nanomedicine. Sep. 2006; 1(3): 297-315.*
Dass, C.R., "Selective gene delivery for cancer therapy using cationic liposomes: In vivo proof of applicability", Journal of Controlled Release, 113, (2006), pp. 155-163.
Ferguson, M.S., et al., "Systemic Delivery of Oncolytic Viruses: Hopes and Hurdles", Advances in Virology, vol. 2012, Article ID 805629, (2012), 14 pages.
Green, N.K., et al., "Extended plasma circulation time and decreased toxicity of polymer-coated adenovirus", Gene Therapy (2004), 11(16), Jun. 24, 2004, pp. 1256-1263.
Kanvera, A., "Adenoviruses for treatment of cancer", Annals of Medicine, 37(1), (2005), pp. 33-43.
Kim, P.-H., et al., "The effect of surface modification of adenovirus with an arginine-grafted bioreducible polymer on transduction efficiency and immunogenicity in cancer gene therapy", Biomaterials, 31, (2010), pp. 1865-1874.
Shimizu, Taro, et al., "Intavenous Administration of Polyethylene Glycol-Coated (PEGylated) Proteins and PEGylated Adenovirus Elicits an Anti-PEG Immunogolbulin M Response", Biol. Pharm. Bull., 35(8), (2012), pp. 1336-1342.
Shoua, I.B., "Development of liposomal formulations to increase the delivery of chemotherapeutic agents, and the possibility of overcoming multidrug resistance", A Cand.Biol.Sci.: 14.00.14.—Moscow,(2005), 109 pages.
Singh, R., et al., "Artificial envelopment of nonenveloped viruses: enhancing adenovirus tumor targeting in vivo", The FASEB Journal, (2008), 22(9), pp. 3389-3402.
Smith, T.A., et al., "Adenovirus serotype 5 fiber shaft influences in vivo gene transfer in mice", Human gene therapy, May 20, 2003, 14(8), pp. 777-787.
Yotnda, P., et al., "Bilamellar Cationic Liposomes Protect Adenovectors from Preexisting Humoral Immune Responses", Molecular Therapy, (Mar. 2002), vol. 5, No. 3, pp. 233-241.
Zheng, Meng, et al., "Lipoic Acid Modified Low Molecular Weight Polyethylenimine Mediates Nontoxic and Highly Potent in Vitro Gene Transfection", Mol. Pharmaceutics, 8, (2011), pp. 2434-2443.
Zhong, Z., et al., "Anionic Liposomes Increase the Efficiency of Adenovirus-Mediated Gene Transfer to Coxsackie-Adenovirus Receptor Deficient Cells", Molecular Pharmacuetics, vol. 7, No. 1 (2010), pp. 105-115.
Zhong, Z., et al., "Anionic Liposomes Enhance and Prolong Adenovirus-Mediated Gene Expression in Airway Epithelia in Vitro and in Vivo", Mol. Pharmaceutics, 8, (2011), pp. 673-682.
Zhong, Z., et al., "Improvement of adenoviral vector-mediated gene transfer to airway epithelia by folate-modified anionic liposomes", International Journal of Nanomedicine, 6, (2011), pp. 1083-1093.

* cited by examiner

COMPOSITION OF VIRAL VECTORS IN LECITHIN LIPOSOMES, PREPARATION METHOD AND TREATMENT METHODS

PRIORITY CLAIM AND REFERENCE TO RELATED APPLICATION

This application claims priority under 35 U.S.C. § 119 from prior provisional application Ser. No. 61/719,574, which was filed Oct. 29, 2012.

STATEMENT OF GOVERNMENT INTEREST

This invention was made with Government support under CA 153915 awarded by the National Institutes of Health. The Government has certain rights in the invention.

FIELD

A field of the invention relates to enhanced viral gene therapy, including cancer therapy. Example applications of the invention include biotechnology drugs in which adenoviral vectors are encapsulated into non-toxic lecithin liposomes, methods for preparing and purifying the encapsulated vectors, and methods in which the encapsulated vectors are used to treat patients.

BACKGROUND

Oncolytic viruses (OVs) are promising agents to combine with nanoparticle delivery approaches because of the capacity for self-replication of the virus. In systemic delivery, targeting with nanoparticles may focus the viral load to the primary tumor cells as well as metastatic tumors to insure a productive initial infection. A single viral particle delivered to a tumor cell can replicate to become thousands of viral particles and induce cell lysis with subsequent infection of additional tumor cells.

Oncolytic viruses can be directed at several mechanisms of action and exploit validated genetic pathways known to be deregulated in many cancers and are directly cytolytic. Cancer gene therapy holds great promise due to the approach which takes advantage of the virus' ability to replicate within cancer cells to levels that are many logs higher than the input dose, lyse the infected cell and subsequently spread to adjacent cells.

Adenoviruses are commonly used in gene therapy for cancer due to their ability to infect a broad range of cells. Recombinant adenoviruses are predominantly derived from adenovirus serotype 5 (Ad5). Clinical evidence of therapeutic activity has been demonstrated for oncolytic virus, ONYX-015. Following initial positive preclinical studies, phase I, II, and III clinical trials of ONYX-015 have been conducted in head and neck, gastrointestinal, ovarian, brain, pancreatic and breast cancer as well as oral dysplasia using local injections. In particular, the oncolytic virus TAV-255 has shown improved viral replication attenuation in normal cells while retaining cytolytic activity in tumor cells by taking advantage of defects in the p53-tumor suppressor pathway.

Despite these advantages, the utility of OVs for cancer therapy, including metastatic cancer, is limited by 1) the lack of expression of surface receptors (CAR) for the most common OVs in certain cancers, 2) rapid clearance by the reticuloendothelial (RE) system in the liver and 3) neutralization by antibodies.

Although high transduction is achieved for CAR positive and CAR deficient cells in positively charged polymer coated Ad, it has been shown that cationic liposomes and polymeric particles are readily taken up non-specifically by various cells.

Furthermore, cationic lipids such as N-(2-hydroxyethyl)-N,N-dimethyl-2,3-bis(tetradecyloxy)-1-propanaminium bromide (DMRIE) and 3β-[N-(dimethylaminoethane)carbamoyl]cholesterol (DC-Chol) have been tested in clinical trials but the resultant biological (therapeutic) effects with these vesicles were at best marginal, and the formulations were hampered by toxicity.

Bilamellar cationic liposomes have shown to protect adenovectors from preexisting humoral immune responses. However, a high distribution in the lungs and liver after i.v injection was exhibited. Similarly, artificial envelopment of nonenveloped viruses showed an extended blood circulation times following i.v. administration and reduced vector immunogenicity. Although this platform allows for an extended circulation time in the bloodstream and a reduced immune response due to PEGylation, more than 70% of virus in the cationic DOTAP:DOPE:DSPE-PEG liposomes was cleared from the bloodstream and accumulated in the lungs, liver and spleen within 5 minutes.

Finally, a surface masking technique was developed. It is based on multivalent copolymers of poly(N-(2-hydroxypropyl)methacrylamide) (HPMA) to ablate all pathways of receptor-mediated infection, combined with dose modulation to achieve partial saturation of nonspecific uptake pathways. Administration of elevated doses of the polymer-coated virus showed an increase in blood circulation time. However, it also showed saturation of phagocytic liver capture. Furthermore, differences in the circulation times between naked Ad and HPMA-Ad in the bloodstream were not distinguishable until they reached higher doses. Since most adults have neutralizing antibodies against Ad, attempts to increase exposure levels through the administration of high doses of Ad vectors can lead to severe liver damage and therefore, high doses should not be administered.

Despite these limitations, marked clinical responses have been observed in some patients following treatment by local as well as systemic delivery, indicating that effective approaches to maximize viral exposure to the tumor cells could enhance the effectiveness of oncolytic viruses as a therapeutic agent.

Although local, intratumoral administration of adenovirus (Ad) has produced marked antitumor effects in cancer gene therapy, there remains a need to develop an Ad vector system for systemic administration that can be used to treat both primary and metastatic tumors.

Several drawbacks are attributed to rapid clearance of the virus from circulation before it can reach its target site in a tumor or metastases. FIG. 1 depicts methods for biotechnology drugs comprising viral particles previously known in the art.

As shown in FIG. 1A, clearance from the bloodstream is mediated through neutralizing antibodies, inflammatory responses, as well as a nonspecific uptake by other tissues such as the lung, liver, spleen, and suboptimal viral escape from the vascular compartment. When viral particles, shown as spiked hexagons, are injected into a blood vessel, they are detected by patient's antibodies, shown as Y. After filtration by the liver, the concentration of viral particles in blood has decreased. Over 80% are accumulated in the liver 10 min after administration and only very few viral particles actually remain in circulation to reach the target tumor cells.

A range of methods have been designed to overcome these limitations. In general, encapsulation of a virus with a cationic liposome or coating the viral capsid with a cationic polymer has been employed due to the net negative charge of the viral capsid. For example, surface modification of adenovirus with an arginine-grafted bioreducible polymer has been developed to improve transduction efficiency and immunogenicity in cancer gene therapy as shown in FIG. 1B. A surface modification method of adenovirus with an arginine-grafted bioreducible polymer has been developed to improve transduction efficiency and immunogenicity in cancer gene therapy. However, the efficacy of viral particles encapsulated in cationic particles is limited by low cell and tissue specificity.

These modified viral particles are primarily taken up by Kupffer cells in the liver and non-specific cells in other organs before the viral particles can reach cancer cells.

Encapsulation of negatively charged adenovirus in cationic liposomes has been used in the field to overcome rapid clearance from the circulation to evade the immune barrier. However, despite the promising in vitro results, cationic liposomal encapsulation in vivo has been hindered by toxicities, low tissue specificity, and poor serum stability due to incompatibility with the abundance of negatively charged macromolecules present in the physiological environment.

Recent studies reported that anionic liposomes enhance transfection in CAR deficient cells. Zhong et al. demonstrated that adenovirus encapsulated in anionic liposomes using a calcium-induced phase change method was capable of protecting adenovirus from neutralization (Zhong et al. Mol. Pharmaceutics, 2011). Zhong et al. also showed that anionic liposomes enhance and prolong adenovirus-mediated gene expression in airway epithelia (Zhong et al., Int. Journal of Nanomedicine, 2011).

INVENTION SUMMARY

This and other needs are addressed by the compositions and methods provided in this disclosure. A composition is provided comprising a recombinant viral particle comprising a capsid, wherein the viral particle is encapsulated into an anionic liposome comprising lecithin and polyethylene glycol (PEG). In some embodiments, the recombinant viral particle is an adenovirus. At least in some embodiments, the anionic liposome further comprises cholesterol.

Included are compositions in which the anionic liposome is a self-assembled lecithin phospholipid bilayer with cholesterol and PEG incorporated in the bilayer. Further included are compositions in which the bilayer has an inner leaflet and an outer leaflet, the inner leaflet interacts with the capsid and PEG moieties are at the surface of the outer leaflet. In the compositions, the viral particle may carry a therapeutic gene. Further included are compositions in which a recombinant nucleic acid is situated inside of the viral particle and encodes an anticancer or therapeutic viral vector.

A method is also provided for preparing a formulation comprising a viral particle encapsulated in an anionic liposome. In the method, a mixture is prepared by dissolving lecithin, cholesterol and PEG in an organic solvent. The mixture is then vacuum-dried to form a dry lipid film. The dried lipid film is then mixed with viral particles and the mixture is hydrated by being put in contact with a physiological solution so that multilamellar vesicles are formed. The multilamellar vesicles are then sonicated and a formulation is formed in which viral particles are encapsulated in anionic liposomes comprising lecithin, PEG and cholesterol.

A method for preparing a purified formulation of viral particles encapsulated in anionic liposomes comprising lecithin, PEG and cholesterol is also provided. In the method, the encapsulated viral particles are purified by immunoprecipitation. At least in some embodiments, the immunoprecipitation is performed with anti-hexon IgG. In other embodiments, the immunoprecipitation can be performed with an antibody raised against any other capsid protein, such as for example, penton or fiber.

Methods for treating a patient are also provided. In the methods, viral particles which carry a therapeutic gene are prepared and encapsulated in liposomes comprising lecithin, cholesterol, and PEG. The encapsulated particles are then administered to the patient.

BRIEF DESCRIPTION OF THE DRAWINGS

FIG. 3A-3C illustrates a purification method in which viral particles encapsulated in liposomes are purified by immunoprecipitation (IP); wherein FIG. 3A is a schematic of an IP technique in which non-encapsulated viral particles are extracted from solution; FIG. 3B is a TEM image of Ad-GFP stained with uracyl acetate; and FIG. 3C illustrates an improved transfection efficiency for encapsulated adenovirus which was purified by immunoprecipitation;

FIG. 7A-7B illustrates neutralization by plasma antibodies of viral particles not encapsulated in lecithin/PEG liposomes; wherein FIG. 7A illustrates that Ad5-eGFP was incubated with mouse plasma containing high titer of neutralizing antibodies and added to A549 cells at MOI 50. The working concentration for neutralization is between $\frac{1}{8}$-$\frac{1}{256}$ since high concentrations of serum (1×, ½×, ¼×) resulted in cell death and low concentrations ($\frac{1}{512}$, $\frac{1}{1024}$ and below) resulted in incomplete or no neutralization; and FIG. 7B illustrates that eGFP expression at MOI 50 is detected for Ad5-eGFP when no nAbs are present;

DETAILED DESCRIPTION OF THE PREFERRED EMBODIMENTS

Figure 1A:
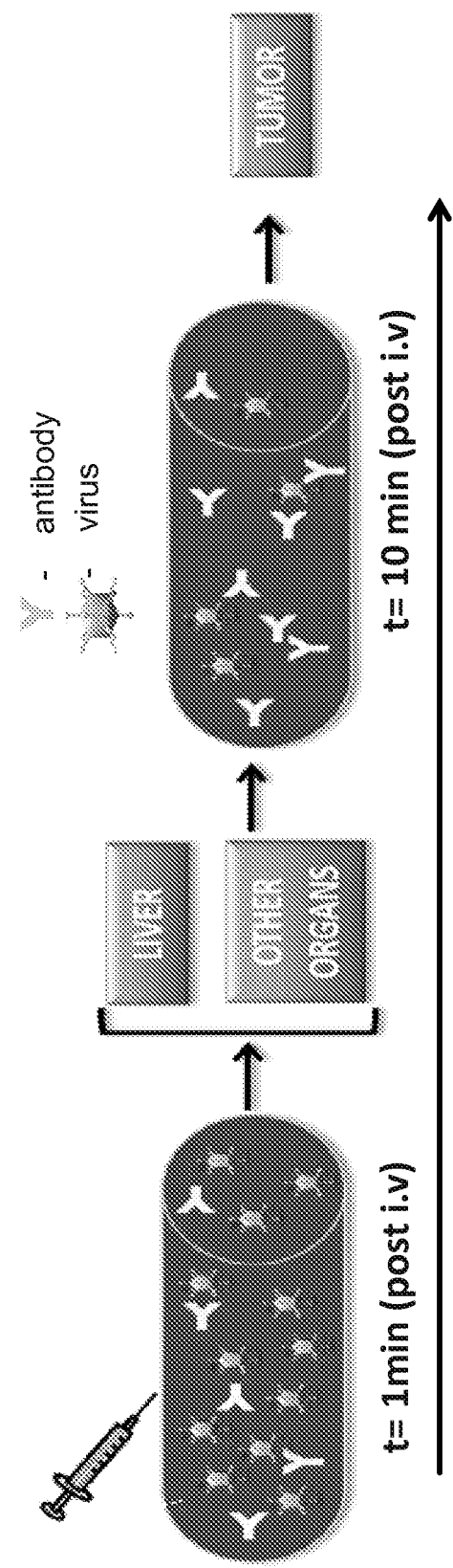
FIG. 1A illustrates that a non-encapsulated oncolytic virus is rapidly cleared by neutralization antibodies and by Kupffer cells in the liver.
Figure 1B:
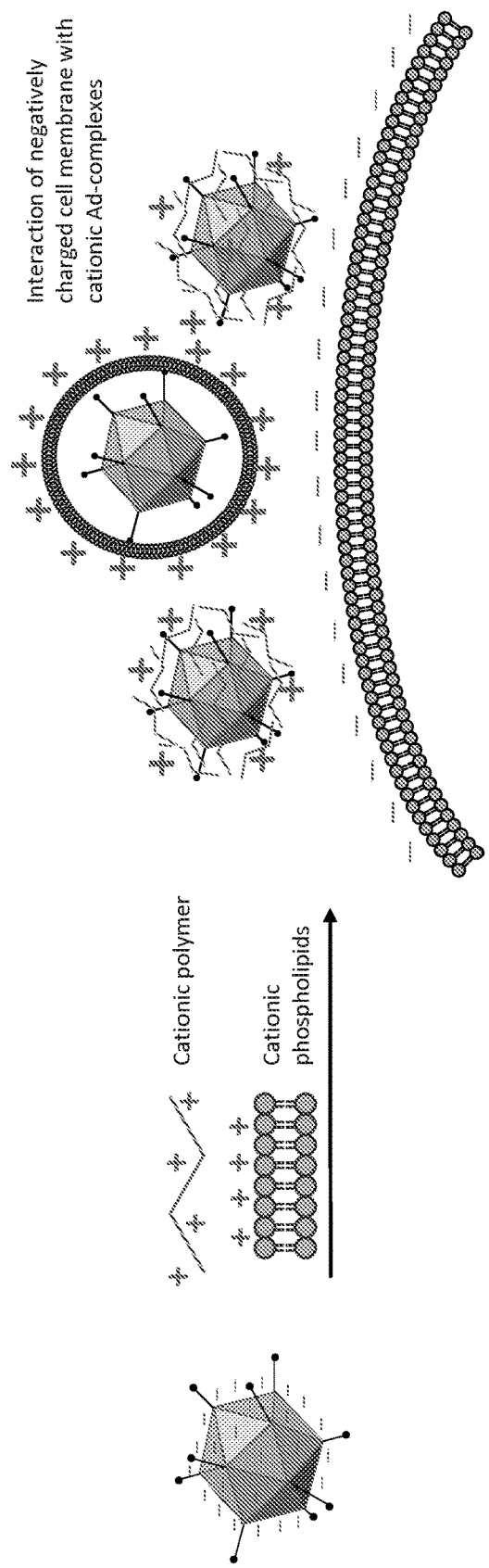
FIG. 1B illustrates a prior art surface modification method of adenovirus coated with a cationic polymer or phospholipid.

Compositions are provided which comprise viral particles encapsulated in anionic liposomes, comprising lecithin and polyethylene glycol (PEG). Compositions are also provided which comprise viral particles encapsulated in anionic liposomes, comprising lecithin, cholesterol, and polyethylene glycol (PEG).

Compositions of the invention are suitable for administration to a patient and can be used in treating patients from a variety of diseases, including cancer, metastatic cancer, cardiovascular disease, neurodegenerative disorders, and infectious diseases. Suitable viral particles include various recombinant viruses such as oncolytic recombinant viruses that are employed in gene therapy. These viral particles may be used in a form of a fully assembled capsid comprising viral proteins, where the capsid encloses and shells a recombinant viral RNA or DNA molecule inside. A recombinant nucleic molecule which is situated inside of the viral particle may carry a therapeutic gene suitable for treatment of cancer or other diseases. A recombinant nucleic molecule may also encode an anticancer or therapeutic viral vector.

In other embodiments, viral particles comprise a capsid which encloses recombinant proteins or any other compound which can be used for treating a patient and needs to be delivered to a particular set of targeted cells in a patient's body. A suitable recombinant viral RNA or DNA molecule may encode for molecules useful in treating a patient, including cytotoxins and antibodies. The targeted cells may include cancer cells or other cells affected by a disorder that can be corrected by gene therapy. In addition to viral proteins, a viral capsid in a viral particle may also comprise other proteins and molecules, including receptor molecules, markers, receptor ligands, dyes and the like. Suitable oncolytic viruses include recombinant adenoviruses, including those recombinant adenoviruses which are based on adenovirus serotype 5 (Ad5).

In addition to a viral particle, the composition comprises an anionic liposome which encloses and encapsulates the viral particle. The anionic liposomes comprise lecithin and polyethylene glycol (PEG). In further embodiments, the anionic liposomes also comprise cholesterol. At least in some embodiments, lecithin, cholesterol and PEG can be formulated in respective molar ratios 2:1:0.1. In addition, different molar ratios containing the same composition may be used for encapsulation. Suitable grades of PEG include DSPE-PEG2000. Shorter and longer grades of PEG chains may be used to optimize circulation time and uptake in cells.

Various formulations of lecithin can be used in the anionic liposomes. Lecithin may comprise zwitterionic and anionic lipids. Suitable lecithin formulations may include lecithin which comprises at least one of the following phospholipids: phosphatidyl choline, phosphatidyl ethanolamine, phosphatidyl inositol and any combination thereof. In some embodiments, lecithin may comprise at least 5% phosphatidyl choline. Lecithin may comprise at least 10% phosphatidyl choline. Lecithin may comprise at least 20% phosphatidyl choline. Lecithin may comprise other phospholipids in addition to phosphatidyl choline. At least in some embodiments, lecithin comprises from 10-30% phosphatidyl choline, from 10 to 30% phosphatidyl ethanolamine, from 10 to 20% phosphatidyl inositol and up 40% other phospholipids. At least in some embodiments, lecithin comprises 24% phosphatidyl choline, 20% phosphatidyl ethanolamine, 14% phosphatidyl inositol and 40% other phospholipids. Lecithin can be obtained from various sources, such as for example soy beans or sunflower seeds. A chemical structure for at least one lecithin species, phosphatidylcholine is provided below:

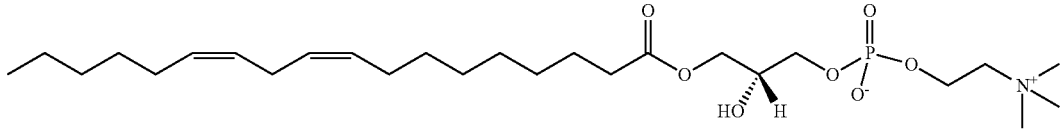

Structure of predominant species

Adding PEG, such as for example, DSPE-PEG2000 increases the in vivo circulation time for a viral particle encapsulated in an anionic liposome which comprises lecithin. A structural formula for a DSPE-PEG2000 representative species is provided below:

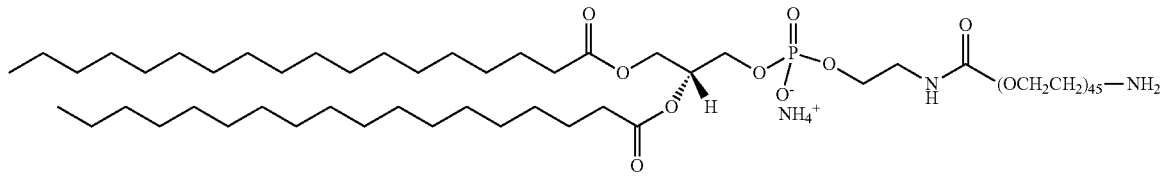

Figure 2A:
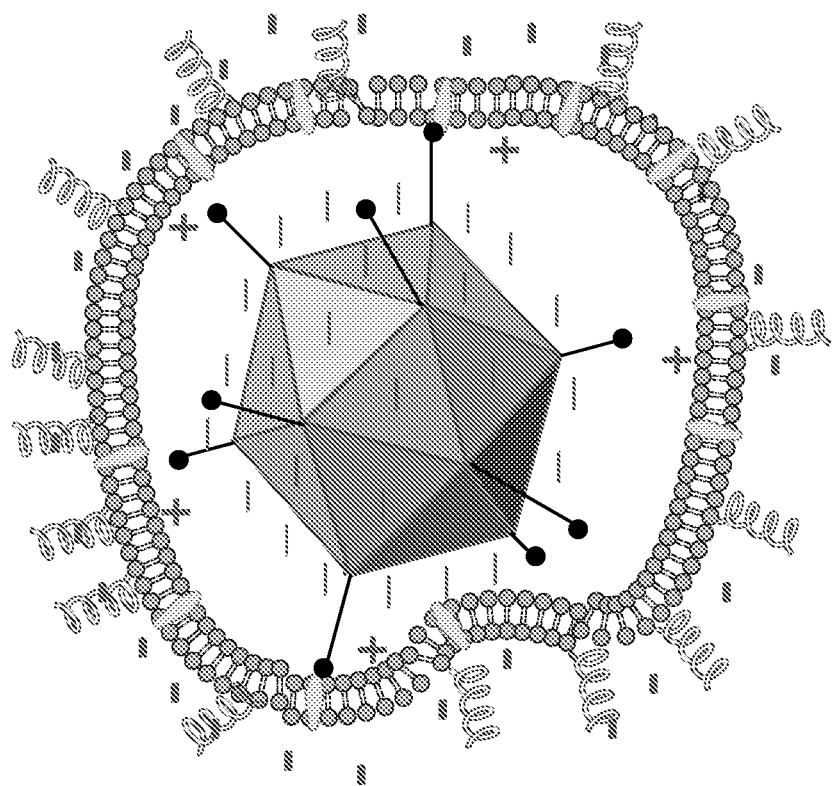
FIG. 2A illustrates an encapsulated virus in which there are electrostatic interactions of phospholipids with a viral capsid.

An exemplary liposome-encapsulated viral particle is shown in FIG. 2A in which a viral capsid, pictured in the center as a rhombus, is encapsulated into a bilayered negatively-charged (anionic) liposome which comprises lecithin and PEG2000. Lecithin is composed of zwitterionic and anionic phospholipids. Zwitterionic phospholipids are shown interacting with the negatively charged viral capsid, which can be an adenovirus or any other negatively charged recombinant virus suitable for gene therapy. The assembly of negatively charged phospholipids such as inositol phosphatides is shown on the outer leaflet of the liposome. This is energetically more favorable due to electrostatic interactions. PEG2000 chains are shown on the outer surface of the liposome complex as protruding wavy lines. It is hypothesized that positively charged amine groups on zwitterionic phospholipids such as phosphotidyl choline and phosphatidyl ethanolamine are interacting with the negatively charged surface of the viral capsid, while anionic phospholipids such as inositol phosphatides are assembling on the outer leaflet of the liposome. The inventors have discovered that an adenovirus encapsulated in PEGylated anionic liposomes can increase the serum stability and PEG chains on the outer surface of the liposome can increase the drug circulation time in the patient's bloodstream during systemic delivery.

Figure 2B:
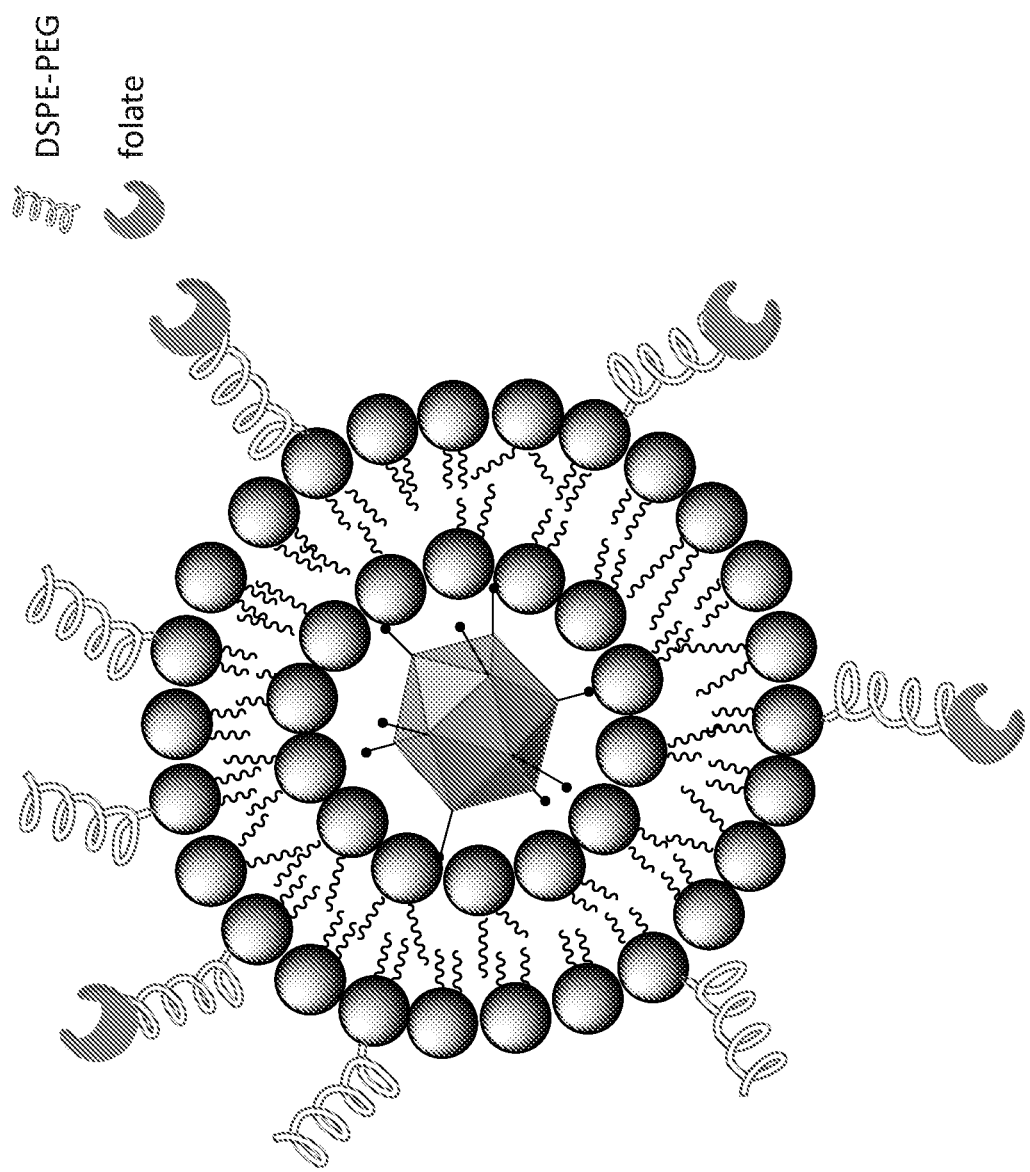
FIG. 2B illustrates an encapsulated virus that bears a folate receptor ligand at the liposome surface.

The inventors have further discovered that liposomal formulations which further comprise a folate ligand presented on the surface of the outer leaflet of the liposome have several surprising advantageous features. FIG. 2B depicts an exemplary folate-modified viral anionic liposome complex in which a virus is encapsulated into an anionic liposome comprising lecithin, cholesterol and PEG. Folate ligands are presented at the surface of the liposome outer leaflet. The surprising advantages of liposomic complexes with folate ligands include a significantly increased efficacy for epithelial cells, including lung epithelial cells. At least in some embodiments folate ligands are prepared on outer surface of liposome as a PEG-folate complex. At least in some embodiments, the molar ratios between PEG and folate are between 10:1; 10:3; 10:5; 10:7 or 1:1.

Further embodiments provide methods for preparing viral particles encapsulated in anionic liposomes which comprise lecithin, cholesterol and PEG. Additional embodiments also provide methods for preparing viral particles encapsulated in anionic liposomes which comprise lecithin, cholesterol, PEG and folate.

Figure 2C:
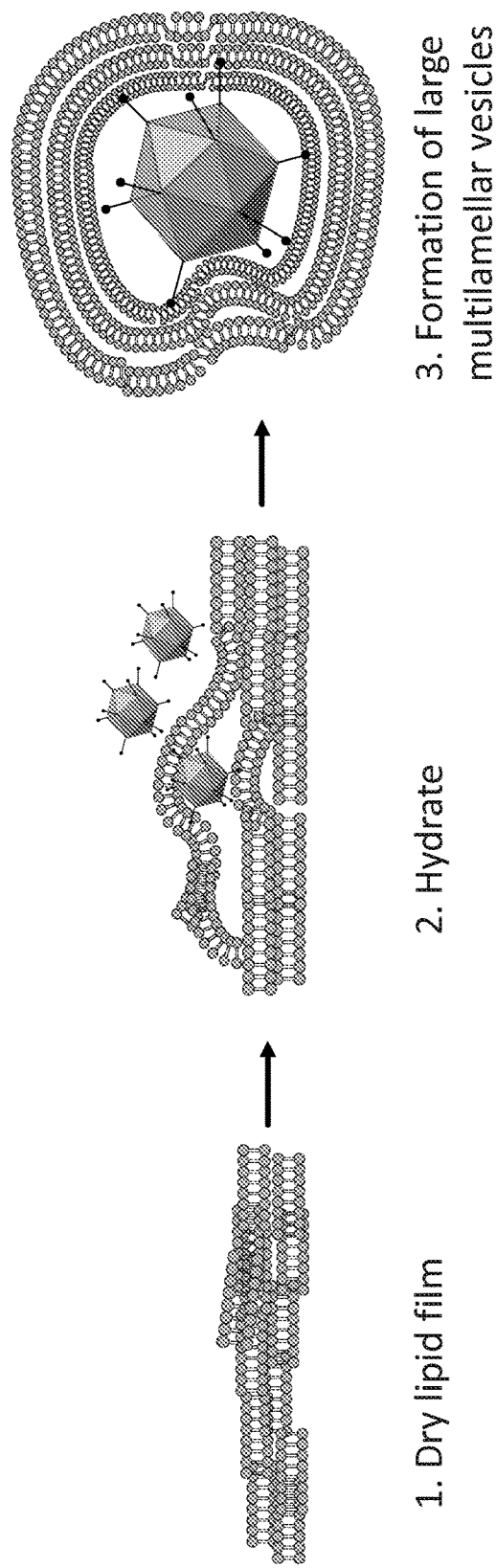
FIG. 2C and FIG. 2D illustrate a thin film hydration technique for preparing viral particles encapsulated in lecithin-PEG liposomes.
Figure 2D:
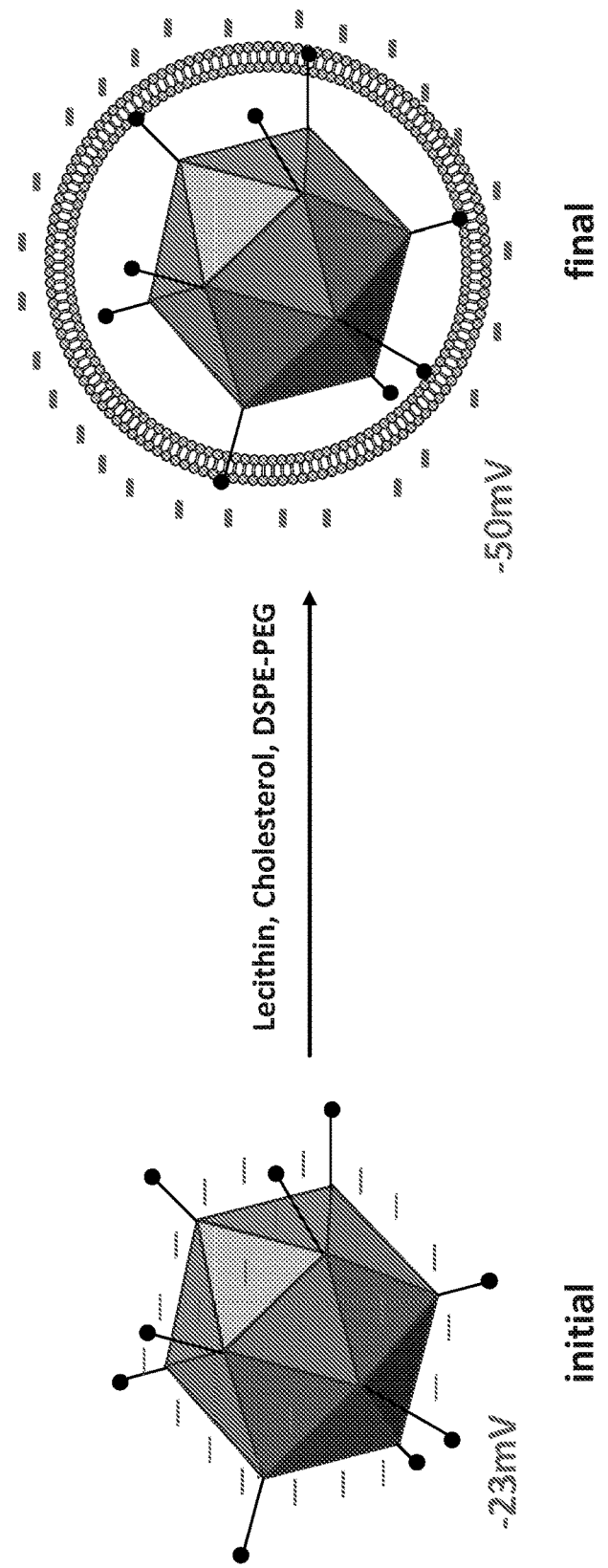

One embodiment provides a lipid film hydration method for preparing encapsulated viral particles. As shown in FIGS. 2C and 2D, lecithin, cholesterol and PEG, such as for example DSPE-PEG2000, are suspended in chloroform or any other solvent suitable for dissolving amphiphilic phospholipids. The molar ratios between lecithin, cholesterol and PEG can be kept at 2:1:0.1. In alternative, the ratios can be increased or decreased to include a larger or smaller proportional amount of lecithin in the mixture. In some embodiments, the mixture further comprises folate which may be added in different amounts. At least in some embodiments, PEG is modified with folate such that at least some PEG moieties at the surface of a liposome are PEG-folate moieties. The molar ratios between PEG and folate may vary and may be 10:1; 10:3; 10:5; 10:7 or 1:1, respectively.

The mixture is then vacuum dried to form a dry lipid film. See FIG. 2C. Viral particles can be added to the dry lipid film. The mixtures are hydrated in any suitable physiological buffer. Such buffer may be PBS (phosphate buffered saline). Other buffers that are well tolerated by a human body can be used as well.

Viral particles can be added in different concentrations depending on the required final effective amount needed for treatment. At least in some embodiments, viral particles are added in the range of $1\text{-}10\times10^{10}$ viral particles. In further embodiments, the particles are added at about $5\text{-}10\times10^{10}$ viral particles and finally in some embodiments, the viral particles are added at $2\times10^{10}$ viral particles.

Upon hydration, multilamellar vesicles (MLV) are formed which may further be sonicated at least in some embodiments to form liposome-encapsulated viral particles as shown in FIG. 2D.

Figure 3A:
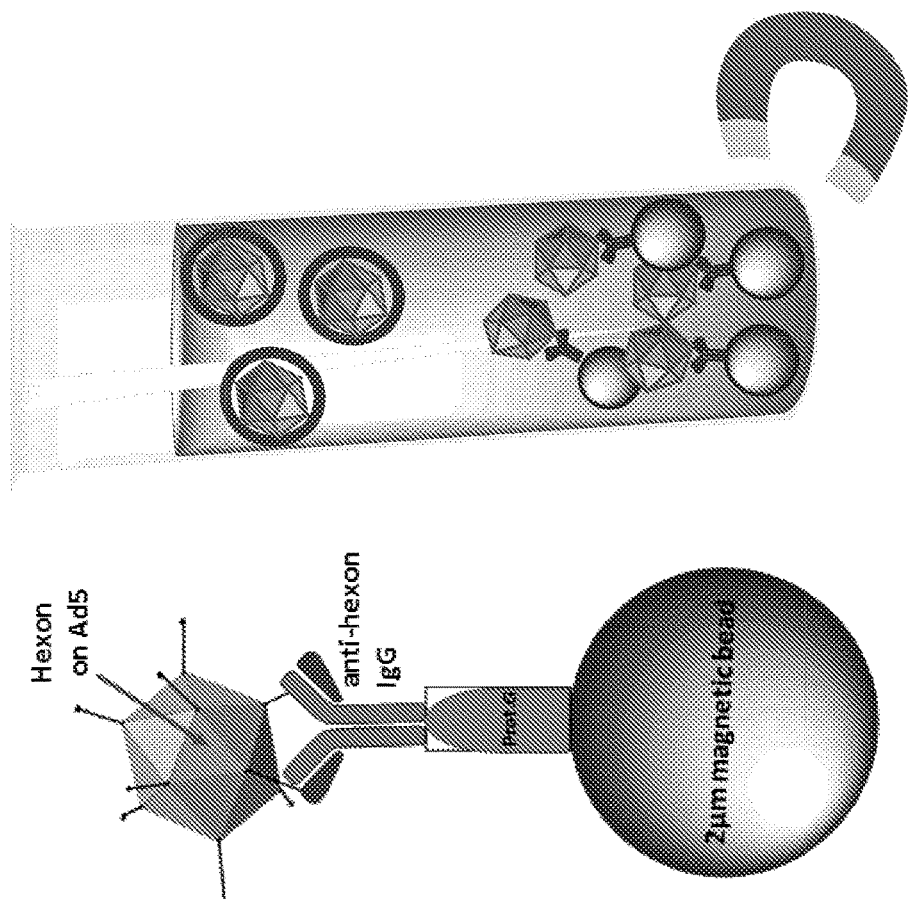
Figure 3B:
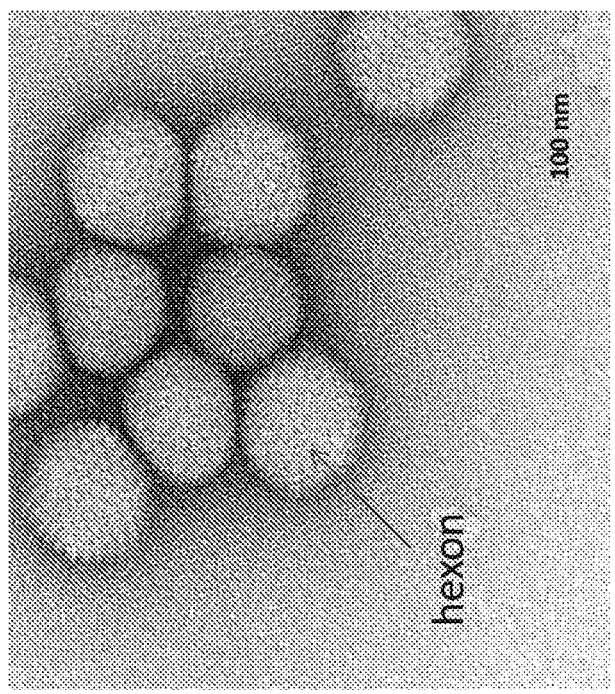

At least in some embodiments, liposome-encapsulated viral particles are further purified by immunoprecipitation (IP). In this method, non-encapsulated viral particles are separated from encapsulated viral particles. As shown in FIG. 3A, encapsulated viruses may be incubated with anti-hexon IgG. Non-encapsulated viruses bound to anti-hexon IgG may then be extracted using Protein G magnetic beads. In alternative, a recombinant virus can be designed such that it expresses an antigen of choice on its viral capsid and then an antibody specific for the antigen can be used instead of an anti-hexon antibody. An antibody which was raised against other viral proteins, such as penton or fiber, can be used instead of an anti-hexon antibody. Further, while protein G magnetic beads can be used in one embodiment, other immunoprecipitation methods can be used in other embodiments.

Figure 3C:
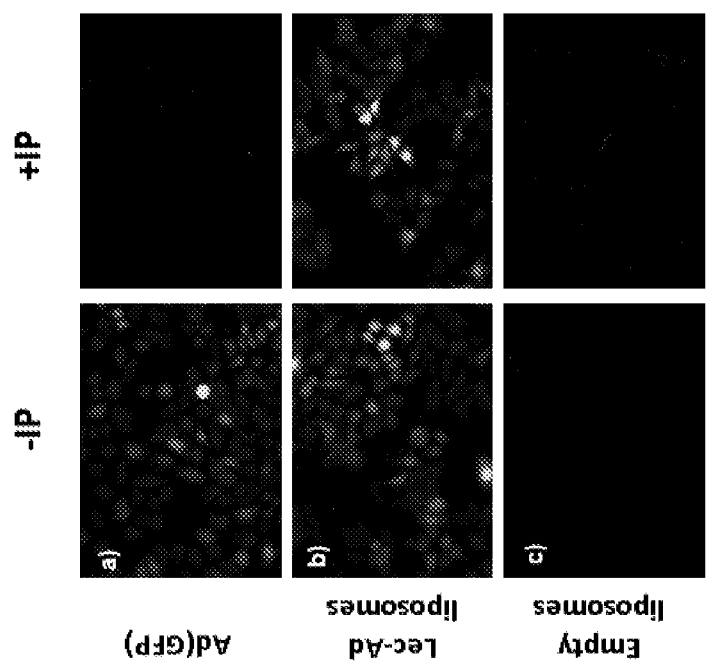

Such methods may include column chromatography, centrifugation and the like. It was discovered that the immunoprecipitation technique also surprisingly reduces the size of encapsulated complexes and homogenizes the sample due to incubation with 2 µm magnetic beads. The inventors have determined that that the IP purification method is highly efficient in separating non-encapsulated viral particles from the encapsulated viral particles. Further, the IP purified encapsulated particles are highly efficient in infecting cancer cells. See FIG. 3C, (−IP panel versus +IP panel). As shown in FIG. 3C, cervical cancer cells were transfected with either non-encapsulated viral particles carrying recombinant gene for GFP protein (Ad(GFP)) or the same viral particles, but encapsulated in lecithin/PEG liposomes (Lec-Ad liposomes). Empty liposomes were used as a control (empty liposomes). Cells were either transfected directly (−IP panel) or viral particles were first purified by immunoprecipitation (+IP panel).

The inventors have also discovered that immunoprecipitation improves a hydrodynamic diameter of encapsulated viral particles and a polydispersity index. In addition to anionic lecithin/PEG liposomes, the inventors also tested cationic liposomes that were prepared with DOTAP.

As shown in Table 1, before immunoprecipitation (−IP), the hydrodynamic diameter of lecithin-liposome encapsulated viral complexes was 180 nm with a high polydispersity index. After immunoprecipitation (+IP), it was unexpected discovered that the viral size was significantly reduced to 143 nm and the liposomes became more monodispersed. These properties were found to be advantageous at least with respect to improving the infectivity in cells targeted for treatment.

TABLE 1

| Sample | Hydrodynamic Diameter (d · nm) | Polydispersity Index (PDI) | ζ Potential (mV) |
|---|---|---|---|
| Adenovirus | 123 ± 6 | 0.1 | −21 |
| Lecithin-Ad −IP | 180 ± 26 | 0.7 | −59 |
| Lecithin-Ad +IP | 143 ± 4 | 0.3 | — |
| DOTAP-Ad −IP | 342 ± 2 | 0.3 | +44 |

TABLE 1-continued

| Sample | Hydrodynamic Diameter (d · nm) | Polydispersity Index (PDI) | ζ Potential (mV) |
|---|---|---|---|
| DOTAP-Ad +IP | 301 ± 2 | 0.3 | — |
| empty Lecithin −IP | 738 ± 38 | 0.6 | −79 |
| empty Lecithin +IP | 138 ± 3 | 0.4 | — |

TABLE 2

| Sample Name | Z-Average (d · nm) | PDI |
|---|---|---|
| Adenovirus | 121 ± 3 | 0.02 |
| Adenovirus (2 days) | 131 ± 1 | 0.1 |
| Lecichin-Ad complex −IP | 229 ± 6 | 0.5 |
| Lecithin-Ad complex −IP (5 d) | 235 ± 6 | 0.5 |
| Lecithin-Ad complex +IP | 142 ± 1 | 0.3 |
| Lecithin-Ad complex +IP (5 d) | 104 ± 5 | 0.4 |

Figure 4:
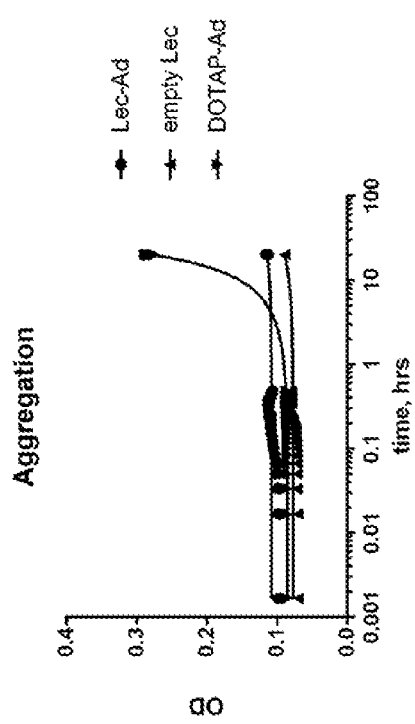
FIG. 4 illustrates serum stability of anionic and cationic liposomes.

The inventors have determined that compositions formulated with anionic liposomes comprising lecithin possess a significantly improved stability in blood serum. As shown in FIG. 4, viral particles encapsulated in anionic liposomes comprising lecithin/PEG were stable in human blood serum for a significant period of time and did not aggregate. This is an improvement over preparations in which viral particles were encapsulated into cationic liposomes and which clump together into larger aggregates as early as at about 2 hours after being contacted with blood serum.

The inventors have also determined that viral particles encapsulated into liposomes comprising lecithin and PEG possess a much higher infectivity in epithelial cells, including lung cancer cells, as compared to the infectivity of viral particles encapsulated into cationic liposomes and viral particles that are not encapsulated.

Figure 5:
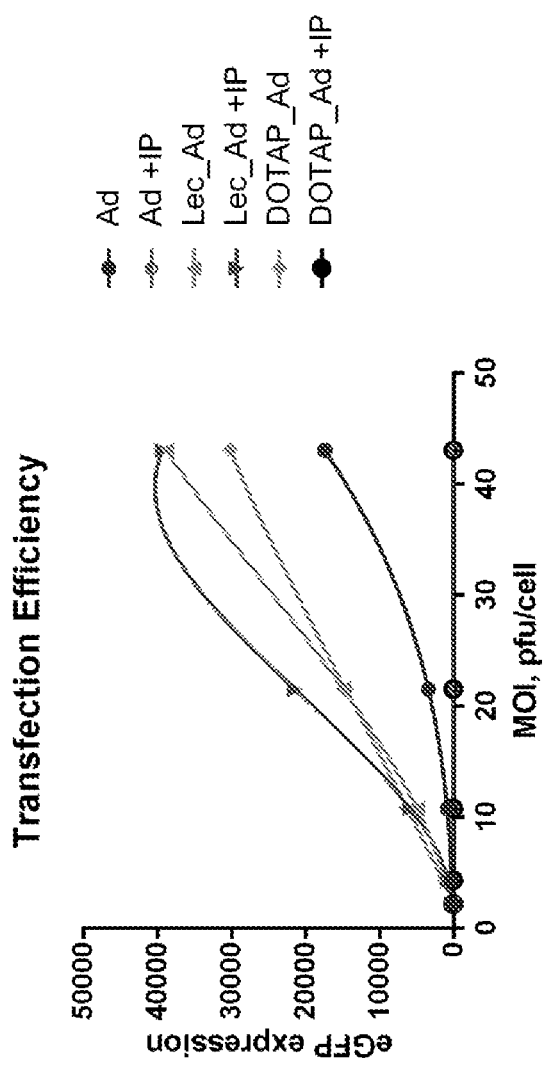
FIG. 5 illustrates improved transfection efficiency of viral complexes encapsulated into anionic liposomes comprising lecithin and IP purified (the Lec_Ad+IP curve) in comparison to viral complexes encapsulated into cationic liposomes (the DOTAP_Ad and DOTAP_Ad+IP curve)

FIG. 5 depicts transfection efficiency in lung cancer cells. As shown in FIG. 5, transfection efficiency of viral particles was significantly improved when the particles were encapsulated into liposomes comprising lecithin and PEG (the Lec_Ad and Lec_Ad+IP curves) in comparison to naked (non-encapsulated) viral particles (the Ad curve) and viral particles encapsulated into cationic liposomes (the DOTAP_Ad and DOTAP_Ad+IP curves). Further, formulations in which liposome complexes were purified by immunoprecipitation had an improved efficiency in comparison to formulations in which liposome complexes were not purified (compare the Lec_Ad+IP curve to the Lec_Ad curve).

Figure 6:
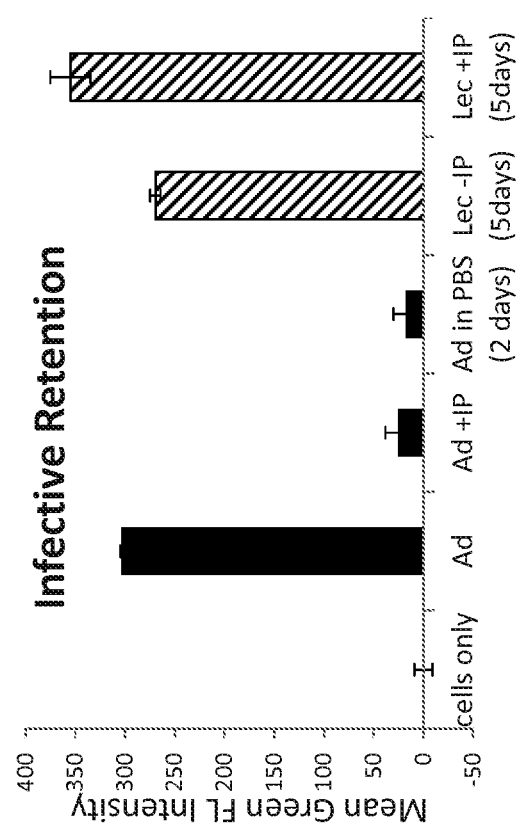
FIG. 6 illustrates retention of infectivity by lecithin/PEG-liposome encapsulated viral particles after being stored at 4° C. for up to five days.

The inventors have discovered that viral particles encapsulated into anionic liposomes comprising lecithin and PEG, retain viral infectivity after being stored in solution for a period of time. This result is unexpected and surprising because non-encapsulated viral particles are highly perishable and lose their infectivity if stored in solution even for a short period of time. FIG. 6 shows that viral particles encapsulated in lecithin/PEG liposomes retained their transfection efficiency after being stored in PBS for more than 5 days (Lec−IP, 5 days and Lec+IP, 5 days). At the same time, non-encapsulated viral particles have lost the infectivity almost completely after storage in solution for only 2 days (Ad in PBS, 2 days).

Surprisingly, encapsulated viral particles which were also purified by immunoprecipitation retained a higher level of infectivity in comparison to encapsulated viral particles which were not purified (Lec+IP, 5 days versus Lec−IP, 5 days in FIG. 6).

The inventors have also unexpectedly determined that there were no significant changes in liposome size after a composition with encapsulated particles was stored for a period of time. Table 2 shows that after 5 days in PBS solution and when stored at 4° C., the size of liposomes was stabilized and the polydispersity has increased only slightly.

Further embodiments provide compositions in which viral particles are encapsulated in lecithin liposomes which express a ligand for a folate receptor. In some embodiments, the folate ligand is made by modifying a DSPE-PEG moiety with folate so that the folate is presented at the outer surface of the lecithin liposome. In some embodiments, all PEG moieties are modified and present folate, in other embodiments only some PEG moieties are modified and bear folate, while other PEG moieties continue to be present at the outer surface of a liposome as unmodified. The inventors have unexpectedly determined that viral particles encapsulated in folate-bearing lecithin liposomes ensures a significantly increased infectivity for certain cells, including cancer epithelial cells. In some embodiments, viral particles encapsulated in folate-bearing lecithin liposomes can be used for selective targeting cells which express a folate receptor. Such cells may include cancer cells. The targeted cells may include lung cancer cells, including non-small lung epithelial cancer cells, breast cancer cells, prostate cancer cells, and colorectal cancer cells.

Figure 8:
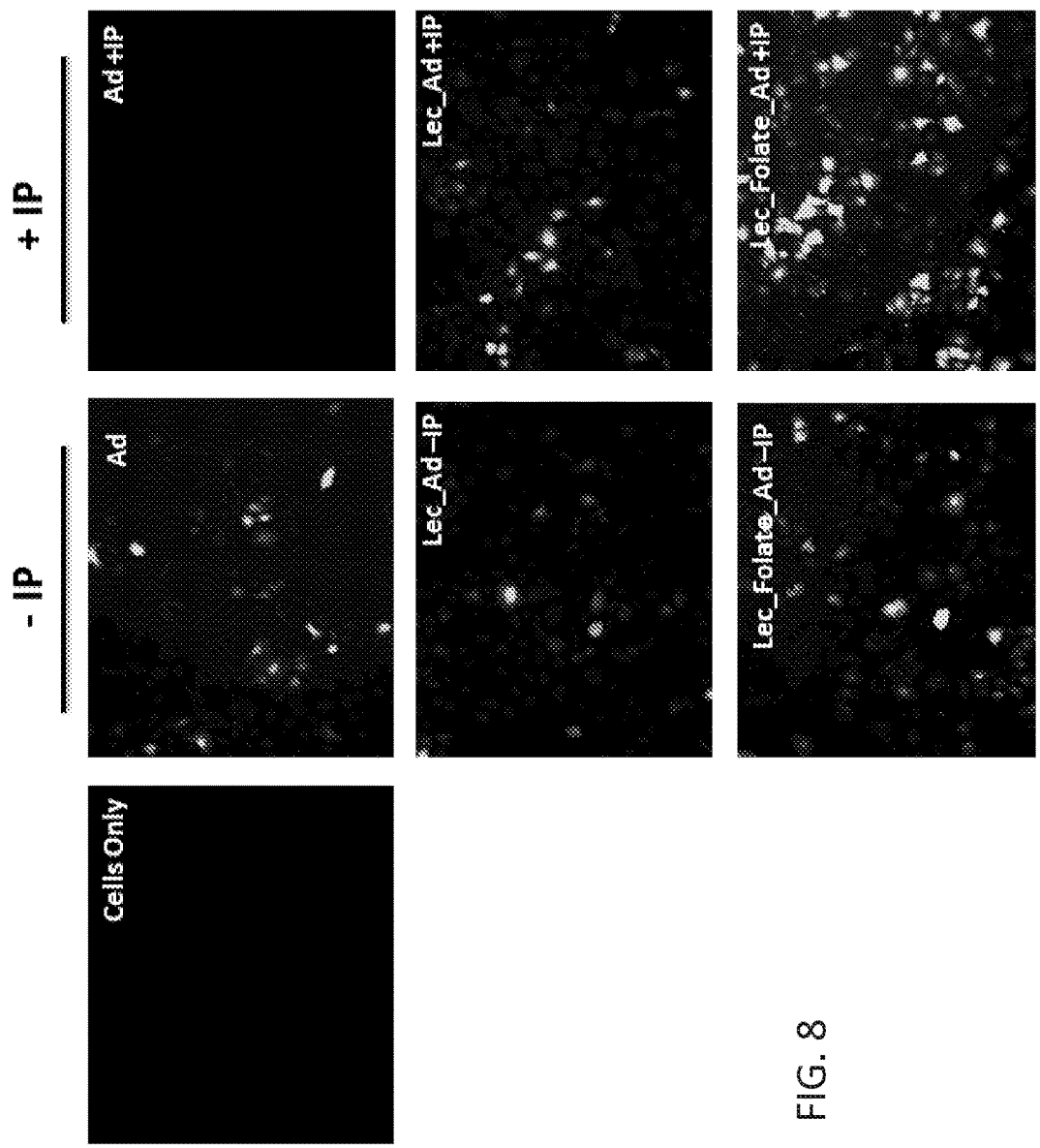
FIG. 8 illustrates a significant increase in infectivity of viral particles encapsulated in lecithin liposomes which bear a ligand for a folate receptor.

FIG. 8 shows a significantly increased infectivity in lung cancer cells with viral particles encapsulated in lecithin liposomes into which DSPE-PEG-folate was incorporated. While folate was used in the embodiment of FIG. 8, other targeting ligands may be incorporated to target surface moieties overexpressed in cancer cells and/or cells of interest which may benefit from gene therapy.

One of the embodiments provides a method for treating cancer in which a patient is administered a composition comprising recombinant virus encapsulated in lecithin liposomes into which DSPE-PEG-folate is incorporated. Patients with various cancers can be treated, including patients who suffer from cancer in which cancer cells express a folate receptor. In one embodiment, cancers that can be treated with a recombinant virus encapsulated in lecithin DSPE-PEG-folate include breast cancer, lung cancer, prostate cancer and colorectal cancer. Compositions in which a recombinant virus is encapsulated into lecithin/DSPE-PEG-folate liposomes can be used for treating other diseases where targeted cells express a folate receptor. Such diseases may include neurological disorders and cardiovascular diseases. In addition various targeting ligands may be utilized to target different mechanisms of entry specifically expressed in target cells.

Figure 9:
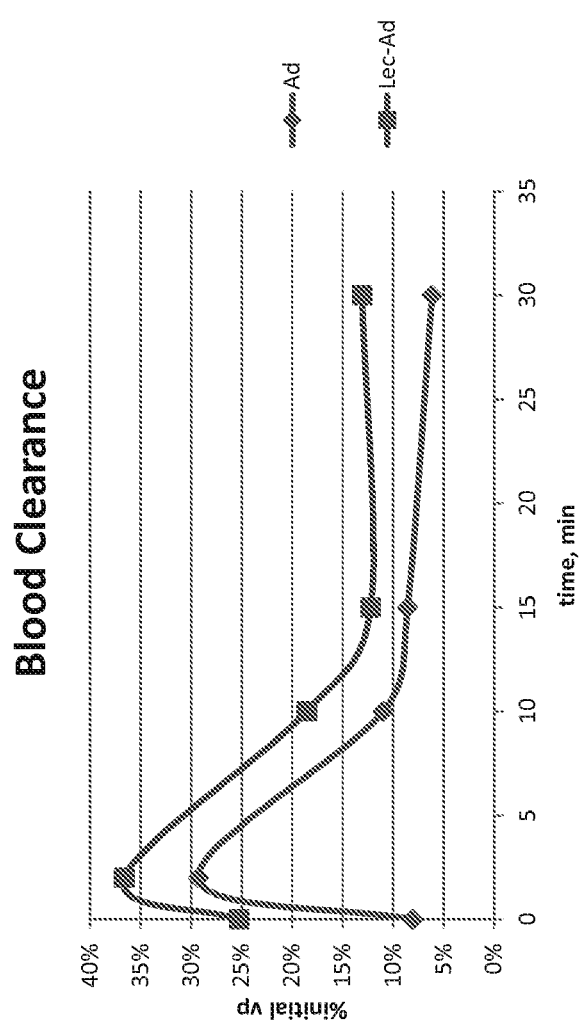
FIG. 9 illustrates clearance of viral particles encapsulated in lecithin liposomes from blood after iv administration.

One of the embodiments provides a method in which viral particles encapsulated in lecithin liposomes are used for systemic delivery of a drug. Such method can be employed in treating various diseases, including metastatic cancers. A person of skill can use any systemic method of delivery known in the art, including intravenous delivery. The inventors have discovered that viral particles encapsulated in lecithin liposomes surprisingly have an improved circulation time in the mammal's bloodstream. FIG. 9 shows that when laboratory mice were injected with viral particles encapsulated in lecithin, the encapsulated particles could be detected in the bloodstream for a longer period of time than viral particles which were not encapsulated (Lec-Ad versus Ad).

Further embodiments include compositions and methods for encapsulating viral drug-delivery vectors. These methods prevent neutralization by antibodies after i.v administration. Encapsulated viruses may extend the blood circulation time allowing accumulation of oncolytic virus in cancer cells including metastasized tumor. These methods minimize an immune response seen in patients due to an acute dose of naked virus administered. The use of narcotic analgesics such as Demoral may not be required if liposomal encapsulation decreases the immune response after administration. The compositions and methods are also provided for a decrease in hepatotoxicity by decreasing uptake of adenovirus in the liver. The compositions of the instant invention can be employed for cancer such as melanoma which do not express the CAR receptor. This can be done by adding targeting to the liposomes.

Disclosed are methods and compositions for liposomal encapsulation of adenovirus useful in oncolytic viral therapy for cancer treatment. The invention overcomes the immune response to increase tumor uptake and enhances therapeutic efficacy of oncolytic viruses in cancer cells. In one embodiment, an inexpensive, non-toxic liposome is prepared by self-assembly of lecithin phospholipid bilayers around an adenovirus capsid. Cholesterol and DSPE-PEG are incorporated into the lipid formulation to improve retention and stability.

Importantly, some embodiments include an immunoprecipitation (IP) technique to effectively and rapidly extract non-encapsulated viruses from solution. The ability to transfect cancer cells is retained after liposomal encapsulation of adenovirus (Ad) and IP processing. The overall procedure has high encapsulation efficiency while retaining viral infectivity.

In one embodiment, the present invention provides liposomes encapsulations that have can provide extended circulation time in the bloodstream due to evasion from non-specific uptake by various cells. Furthermore, liver uptake may be decreased due to this characteristic.

One embodiment provides an encapsulation method of uniform and stable adenovirus (Ad5) in non-toxic lecithin liposomes. Enhanced permeability and retention of nanoparticles (100-200 nm) in tumor cells is achieved more readily compared to normal tissue due to the tumor's leaky vasculature.

In another embodiment, an immunoprecipitation (IP) technique to extract non-encapsulated viruses from solution is also provided. Remaining non-encapsulated viruses due to poor encapsulation efficiency may lead to an adverse immune response and rapid clearance when used in an in vivo model. To prevent this, an IP technique is provided to precipitate free virus. The technique also provides additional advantages such as homogenizing the sample size due to vigorous mixing of the liposome complexes with 2 µm nonporous magnetic beads without decreasing transfection efficiency of encapsulated viruses in liposomes. After IP incubation, liposomes are more homogenous and monodispersed due to the bead-based homogenizing step which further enhances the uptake of liposomes into cells due to the decrease in size.

According to the instant invention, the ability to transfect cancer cells is retained after liposomal encapsulation of adenovirus (Ad) and IP processing. The overall procedure provides high encapsulation efficiency while retaining viral infectivity. Further, Ad is typically administered in saline buffer for therapy, however Ad has shown a loss of infectivity when kept in PBS for several days. Encapsulation of Ad in lecithin liposomes by the provided methods ensures that Ad retains viral infectivity in PBS even after several days. Further, Lecithin-encapsulated Ad is effective in different cancer cells lines.

Artisans will appreciate that preferred embodiments described above include a dry lipid film hydration technique which results in high encapsulation efficiency and high retention of viral infectivity. Furthermore, it is easy to fabricate and affordable. The lecithin liposome-adenovirus vehicle system has the potential to have an extended circulation time in the bloodstream while evading nonspecific uptake by various cells. Furthermore, anionic liposomes protect Ad from antibody neutralization which would further contribute to extending the viruses' circulation time. Also, Ad encapsulated in anionic lecithin liposomes may enhance gene expression in CAR negative cell types making it possible to use in systemic delivery for metastatic tumors.

High toxicity due to non-specific uptake by various cells is observed for cationic (positively charged) drug delivery systems due to a negatively charged cell membrane. Since lecithin liposomes have a net negative charge, their circulation time in the bloodstream is extended due to decreased non-specific uptake by cells. At least in some embodiments, targeting may be employed to reach target of interest (i.e. tumor, organ, etc.).

In some embodiments, a thin lipid film is dried overnight under vacuum and hydrated with $5\times10^{10}$ viral particles/ml (vp/ml). The large multillamelar vesicles are then sonicated and stabilized to form smaller liposomes.

The invention also provides an encapsulation method of uniform and stable recombinant adenovirus serotype 5 (Ad5) in non-toxic lecithin liposomes. According to the method, hydration of the lipid film with phosphate buffered saline (PBS) containing Ad causes phospholipids to self-close due to their amphiphilic behavior. Spontaneous formation of large multilamellar vesicles encapsulating Ad is energetically favorable, where Ad particles serve as a template for liposome formation. Sonication decreases the size of the liposomes without inactivating the viruses' ability to enter cells and replicate or express recombinant proteins. The size and charge of Ad5 and lecithin-Ad5 liposomes were characterized using Dynamic Light Scattering (Malvern, Nano Zetasizer). Data is shown in Table 2. Stability of Ad-liposome complexes was analyzed by measuring liposome size after a week. No major differences in size were observed as shown in Table 2.

At least in some embodiments, the infectivity of viral particles after encapsulation can be monitored by various methods, including encapsulating recombinant adenovirus vector expressing green fluorescent protein (GFP) in lecithin liposomes.

EXAMPLES

Example 1. Materials and Methods

Cell Culture

HeLa human cervical carcinoma cells and A549 human lung carcinoma cells were obtained from the American Type Culture Collection (ATCC, Manassas, Va.). LKR-13 cells were kindly provided by Dr. Reid's laboratory. Cells were cultured with Dulbecco's-modified Eagle's medium (DMEM) supplemented with 10% fetal bovine serum (FBS) and 1% Penicillin Streptomycin Glutamine (PSG).

Synthesis of Lecithin Liposomes Using Lipid Film Hydration Method

Refined Lecithin (Alfa Aesar, Ward Hill, Va.) or DOTAP (Avanti polar lipids, Alabaster, Ala.), Cholesterol (Sigma-Aldrich, St. Louis, Mo.), and DSPE-PEG(2000)carboxylic acid (Avanti polar lipids, Alabaster, Ala.) suspended in chloroform at 10 mg/ml were mixed in 7 ml amber vials at a 2:1:0.1 mM ratio, respectively. The mixtures were placed under vacuum overnight resulting in dry lipid films. The films were hydrated drop-wise while vortexing with 400 µl of adenovirus-CMV-GFP (Baylor College of Medicine, Houston, Tex.) suspended in phosphate buffered saline (1×PBS) at $5 \times 10^{10}$ viral particles/ml (vp/ml). For empty liposomes, lipid films were hydrated with 400 µl of 1×PBS. A small magnetic stirring rod was added, and the hydrated films were stirred for 30 min at 4° C. The samples were subsequently transferred to eppendorf tubes and placed in an ultrasonic water bath (Fisher Scientific, Model FS11011) for 10 min at 4° C. The suspension was allowed to stabilize for 3 h at 4° C. resulting in lecithin-adenovirus liposomes (Lec-Ad), empty lecithin liposomes (empty-Lec), and DOTAP-adenovirus liposomes (DOTAP-Ad).

Immunoprecipitation of Non-Encapsulated Adenovirus 12.5 µl of 1 µg/ml anti-hexon IgG (Thermo Scientific, Rockford, Ill.) was added to 20 µl of Lec-Ad, DOTAP-Ad, or empty-Lec and vortexed at 4° C. for 1 h. 25 µl of 2 µm nonporous superparamagnetic protein G beads (New England BioLabs) were washed with 1 ml of 0.1M sodium biphosphate, resuspended in 80 µl and added to the sample containing anti-hexon IgG mixed with Lec-Ad, DOTAP-Ad, or empty-Lec. The mixture was vortexed for 1 h at 4° C. A magnet was used to pellet the magnetic beads and the supernatant was transferred to a clean, sterile tube. Samples were used for liposome-cell experiments on the same day of preparation.

Viral Titer Determination

HEK293 cells were plated overnight at $1 \times 10^6$ cells/well on 6-well tissue culture plates pre-coated with Collagen (Biocoat, Falcon). 1/10 serial dilutions of Ad or Lec-Ad+IP were prepared and added to cells. The cells were transfected overnight, overlayed with agar, and monitored for plaque formation. At day 11 plaques were stained with 0.1% v/v MTT (Sigma) for 3 hrs at 37° C. and plaque forming units per ml (pfu/ml) was determined. At least two different wells with different serial dilutions were counted to ensure consistency.

Characterization of Liposomes

Liposomes were characterized by dynamic light scattering using Malvern Zetasizer nano series (Model Zen3600, Malvern Instruments, Inc) to measure the size, $\xi$ potential, and polydispersity.

Serum-Induced Particle Aggregation

Human serum (Innovative Research, Novi, Mich.) was incubated in 96-well plates at 37° C. and 5% CO2 for a 1 hr before use. Lec-Ad or DOTAP-Ad liposomes were incubated at a final concentration of 1.4 mg/ml liposome and $5 \times 10^{10}$ vp/ml in 50% human serum and aggregation was monitored by measurement of absorbance at 560 nm at 37° C.

Transfection Efficiency of Adenovirus

HeLa, A549, or CHO cells were plated overnight at $2 \times 10^4$ cells/chamber (1.7 cm$^2$/chamber) (BD Falcon, Bedford, Mass.) for fluorescence microscopy experiments or at $2 \times 10^3$ cells/well in a 96-well plate (Greiner bio-one, Germany) for fluorescence spectroscopy experiments; cultures were incubated at 37° C. and 5% $CO_2$ in DMEM media supplemented with 10% FBS, 1% PSG. Ad5, Ad5-Lec, DOTAP-Ad, and empty_Lec samples before and after immunoprecipitation (−IP, +IP, respectively) were added to cells at a multiplicity of infection (MOI) ranging from 0.43 to 43 and incubated for 48 hours at 37° C. and 5% $CO_2$. For fluorescence microscopy analysis, cells were washed two times in 1×PBS and fixed with 2% Performaldehyde. The slides were sealed with ProLong Gold Antifade reagent (Invitrogen) and imaged using a Zeiss Axio Examiner.Z1 Microscope (AlexaFluor488 filter). For fluorescence spectroscopy analysis, cells were re-suspended in 100 ul of 1×PBS and fluorescence measurements were measured using a Tecan infinite M200 microplate reader at an excitation $\lambda$ of 480 nm and an emission $\lambda$ of 520 nm.

Neutralization Assay of Encapsulated Ad5

Blood was collected from 129/sv mice containing high neutralizing antibodies due to repeated i.t injection of Ad5. Blood was collected in EDTA vacutainers, centrifuged at 25,000 rpm for 15 min and plasma was collected. Plasma was stored at −80° C. until ready for use. A549 cells were plated at 20,000 cells/well in a 96-well plate overnight. Ad5, Lecithin-Ad5, and Lec-Ad5+IP were incubated with anti-adenovirus whole antiserum for 1 hour at 37° C. using ½ serial dilutions. Plasma was first decomplemented for 30 min at 56° C. 100 ul of $1 \times 10^7$ pfu/ml were added to 100 ul of whole serum (1:1) and ½ serial dilutions up to $\frac{1}{1024}$. Samples were added to A549 cells at 50 pfu/cell. Media was changed after 12 hours. Samples were incubated with cells for 24 hours at 37° C. and 5% $CO_2$. Cells were re-suspended in 100 µl of 1×PBS and fluorescence measurements were measured using a Tecan infinite M200 microplate reader at an excitation $\lambda$ of 480 nm and an emission $\lambda$ of 520 nm.

Folate Targeting

Lecithin:Cholesterol:DSPE-PEG2000/folate liposomes encapsulating Ad5 were prepared as mentioned above. The total moles of DSPE-PEG2000 and DSPE-PEG2000-folate was kept constant (0.1 mM); however, the ratio between the two was varied from 0, 0.01, 0.03, 0.05, 0.07, 1 mM.

Circulation Study of Ad5 and Lecithin-Ad5 In Vivo

The blood circulation time of adenovirus and Lecithin-Adenovirus was tested within 30 min at time points t=0 (pre-injection), t=2 min, t=10 min, t=15 min, and t=30 min. Balb/c mice were anesthetized using isoflurane and approximately 100 µl blood was collected in EDTA vacutainers (BD & Co.) at each timepoint. Blood collected from control mice was spiked at ¼ dilutions from $7.4 \times 10^8$-$2.0 \times 10^6$ vp/ml. Blood was spun down and plasma was collected. QIAamp DSP Virus Kit was used for DNA extraction and stored at 4° C. Amplification of an 84 bp fragment of the Adenovirus Fibre gene was carried out using HemoKlen Taq, and the primers 5' TGGCTGTTAAAGGCAGTTTGG 3' (SEQ ID NO. 1) and 5' GCACTCCATTTTCGTCAAATCTT 3' (SEQ ID NO. 2). SYBR green dye was used for detection on the Mx3005p qPCR system (Agilent Technologies, Inc).

Example 2. Encapsulation of Ad5 in PEGylated Anionic Liposomes

Lecithin:Cholesterol:DSPE-PEG2000 and Lecithin:Cholesterol:DSPE-PEG/folate were formulated as described in Example 1. FIG. 2 shows a schematic of Adenovirus 5 being encapsulated in a liposome using the thin film hydration technique. As shown in FIG. 2C, large multilamellar vesicles form after hydration. An immunoprecipitation (IP) technique was developed to clear non-encapsulated viruses to ensure complete encapsulation and the method has shown to precipitate non-coated viruses as well as reduce the size of liposome-Adenovirus 5 complexes. The final encapsulated adenovirus in anionic lecithin/PEG liposomes after IP is shown in FIG. 2A. Due to the net negative charge of the Ad5 capsid, cationic encapsulation is more practical due to favorable electrostatic interactions. However, cationic liposomes have shown to have high toxicities, low serum stability and low tissue specificity. For anionic encapsulation of Ad5, lecithin, a combination of zwitterionic and anionic phospholipids was used. It is hypothesized that zwitterionic phospholipids such as phosphotidylcholine and phosphatidylethanolamine are interacting with the surface of the viral capsid, while anionic phospholipids such as inositol phosphatides are assembling on the outer leaflet of the liposome. FIG. 2A shows an encapsulated Ad5 with PEG chains on the outer surface of the liposome in order to improve circulation times during systemic delivery.

Example 3. Immunoprecipitation of Non-Encapsulated Adenovirus

An immunoprecipitation (IP) technique was developed to extract non-encapsulated adenoviruses from solution. For repeated administration, complete encapsulation of Ad5 is desired in order to reduce antibody production after administration to a patient. In addition, the dose tolerance in patients may be improved by reducing adverse immune responses, thus enhancing OV therapy. After encapsulation in lecithin liposomes, complexes were incubated with anti-hexon IgG antibodies for 1 hr. The antibody recognizes hexon proteins on the surface of Ad5 while encapsulated Ad5 is masked from anti-hexon recognition.

The complex was then incubated with 2 μm magnetic Protein G beads which binds to IgG and non-encapsulated viruses were extracted using a magnet. In addition to extracting non-encapsulated viruses, the immunoprecipitation method also reduced the size of the liposome complexes due to homogenization caused by vigorous shaking of Lecithin Ad5 complexes with 2 μm magnetic beads.

Example 4. Viral Determination after Immunoprecipitation

A plaque forming assay was employed to determine the viral titer before and after encapsulation. The stock adenovirus titer was determined to be $5.6 \times 10^9$ pfu/ml and the viral titer for lecithin-Adenovirus+IP samples was determined to be $7.5 \times 10^6$ pfu/ml. Theoretically, if no viral loss was observed during the immunoprecipitation process, the titer would be measured at $9.9 \times 10^6$ pfu/ml therefore 76% of adenovirus was encapsulated and retained after IP processing.

Example 5. Characterization of Purified Encapsulated Ad5

Size, charge and polydispersity of Ad5 encapsulated in lecithin and DOTAP liposomes were characterized using dynamic light scattering and electrophoretic light scattering as shown in Table 1. The hydrodynamic diameter of naked Ad5 is 123 nm with a negative charge of −21 mV. After encapsulation in lecithin or DOTAP liposomes, the charge is −59 mV and +44 mV, respectively. Before immunoprecipitation (IP), the hydrodynamic diameter of lecithin adenovirus complexes were 180 nm with a high polydispersity index. After IP, the size was reduced to 143 nm and the liposomes became more monodispersed. The IP step was incorporated in order to extract non-encapsulated viruses from solution. In addition to an extraction method, the IP technique also served as a homogenization step. For proof of concept, the size of empty lecithin liposomes were measured before and after IP. The size of empty liposomes was reduced from 738 nm to 138 nm, and the polydispersity was reduced.

Example 6. Serum Stability

Serum stability of anionic lecithin_Ad liposome complexes and cationic DOTAP Ad liposome complexes were assessed in healthy human serum at 1:1 v/v as shown in FIG. 4. There are abundant negatively charged serum components present in serum which caused cationic DOTAP_Ad complexes to aggregate over time; however, Ad5 encapsulated in lecithin liposomes did not aggregate. Empty lecithin liposomes also showed no aggregation due to their net negative charge. All liposome preparations contained PEG and were monitored for a period of time over 20 hours. As shown in FIG. 4, aggregation of particles was observed for cationic liposomes (see the DOTAP-Ad curve), while lecithin-PEG liposomes were stable and did not aggregate (see the Lec-Ad curve for encapsulated virus and the empty Lec curve for empty liposomes).

Example 7. Transfection Efficiency

A549 cells strongly express the Coxsackie virus and Adenovirus Receptor (CAR) which enables entry of Ad5 into the cells and are high permissible. A549 cells were transfected with Ad5, Lecithin_Ad5, or DOTAP_Ad5 before and after immunoprecipitation (IP) at MOI 2.2, 4.3, 10.75, 21.5 and 43 pfu/ml as shown in FIG. 5. After IP, eGFP expression was reduced to zero which showed the IP method was effective in extracting non-encapsulated viruses. At higher MOIs, the transfection efficiency of Ad5 was enhanced when encapsulated in the anionic PEG liposomes. Ad5 encapsulated in Lecithin PEG liposomes after IP (Lec_Ad+IP) was the most effective at transfecting cells most likely due to reduction of size and homogenization after immunoprecipitation. In addition, anionic liposomes enter through an alternative endocytotic pathway which may be more effective and more abundant than the CAR receptor. Before IP, Ad5 encapsulated in DOTAP was effective; however, after IP, eGFP expression was reduced to cells only signal. This suggests that adenovirus encapsulated in DOTAP is not fully encapsulated or that the IP step is disrupting the cationic liposome layers due to some charge interactions but not affecting anionic liposomes.

Example 8. Infective Retention of Encapsulated Ad5

The retention of viral infectivity and transfection efficiency of Ad5 in lecithin liposomes were evaluated after 5 days as shown in FIG. 6. When Ad5 was stored in PBS at 4° C. for even just 2 days, its transfection efficiency was completely lost, as can be seen by transfection of epithelial cells A549 at day 2 post-storage (Ad in PBS, 2 days). However, when Ad5 was encapsulated in liposomes comprising lecithin and PEG and stored at 4° C., the transfection efficiency was retained within at least 5 days. In addition, the size distribution of the liposomes before immunoprecipitation remains the same over several days and the size of liposomes after IP is stabilized after several days however the polydispersity is slightly increased as shown in Table 2, where measurements of liposomes were taken at day 1 and day 5 and un-enacapsulated virus was measured on day 1 and day 2.

Example 9. Neutralization Assay

Figure 7A:
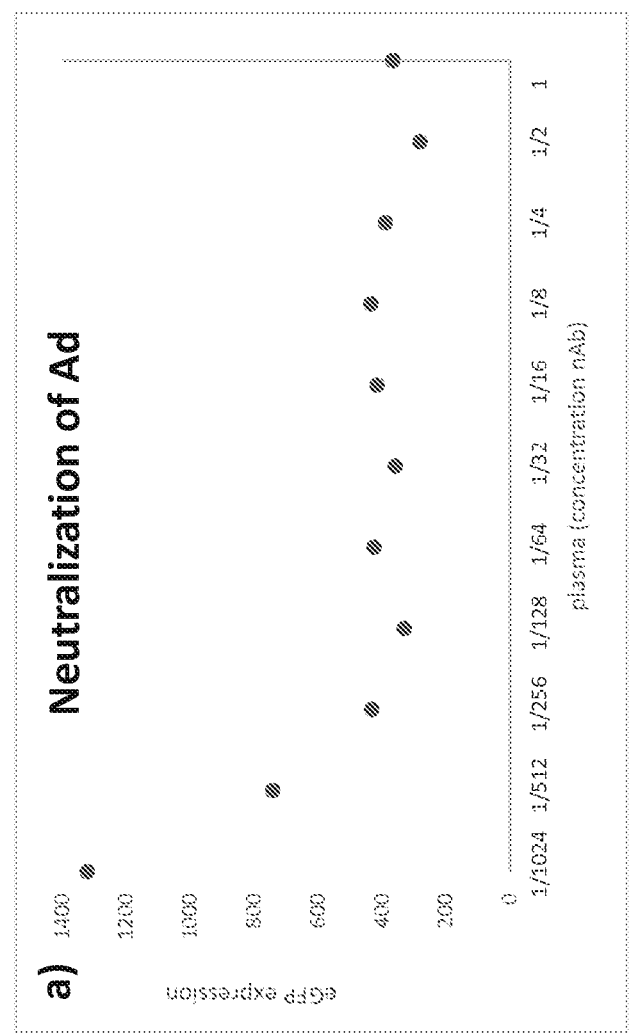
Figure 7B:
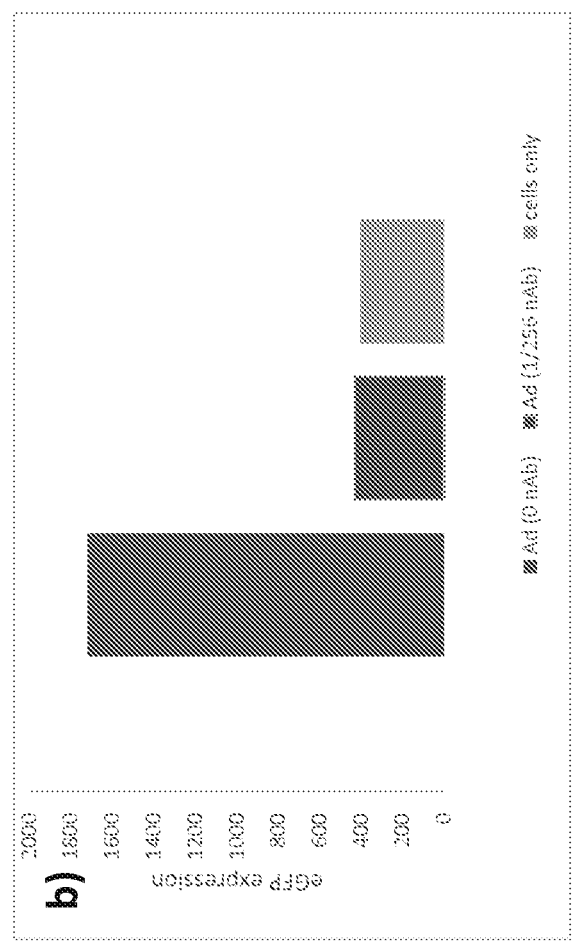

Mice were injected with TAV-255 (Ad5-eGFP) recombinant virus every three days for three weeks and terminally bled. Plasma which contained a high neutralizing antibody (nAb) titer was collected, decomplemented, and incubated for 1 hour at 37° C. with Ad5 at ½ dilutions at a 1:1 v/v concentration of MOI 50 and added to cells. Significant cell death was observed at high concentrations of plasma (1×, ½×, and ¼×) when added to cells; therefore plasma should be diluted to at least ⅛ to maintain physiological conditions and prevent cell death for neutralization assay. The working concentration for neutralization of Ad5 should be between ⅛-1/256 as shown in FIG. 7A. FIG. 7b shows that Ad5 can transfect in the absence of serum, but is completely neutralized when incubated with serum containing nAb at a 1/256× dilution. At higher dilutions, nAbs present in serum do not neutralize Ad5 completely.

Example 10. Folate Receptor Targeting

DSPE-PEG-folate was incorporated into Lecithin Ad5 liposomes during the dry lipid film step. Folate is known to be overexpressed in many cancer cells. 74% of adenocarcinomas (NSCLC subtype) exhibit positive folate receptor a expression which make folate an attractive targeting ligand. A549 cells were transfected with Ad, Lecithin_Ad, and Lecithin-folate_Ad before and after IP. Ad5 encapsulated in Lecithin-folate liposomes showed a significance increase in cell uptake and eGFP expression after immunoprecipitation as shown in FIG. 8. This may be due to the synergy of reduced size of the liposome due to IP processing and targeting.

Example 11. Circulation Study of Ad5 Encapsulated in Lecithin Liposomes

In order to evaluate the circulation time of adenovirus encapsulated in lecithin liposomes after IP, viral particles were detected at timepoints t=0 (pre-injection), 2, 10, 15, and 30 min after i.v injection. The encapsulated viruses appeared more persistent and a higher concentration remained circulating in the bloodstream for a longer period of time as shown in FIG. 9.

Example 12. Infectivity in HeLa Cells

Figure 10:
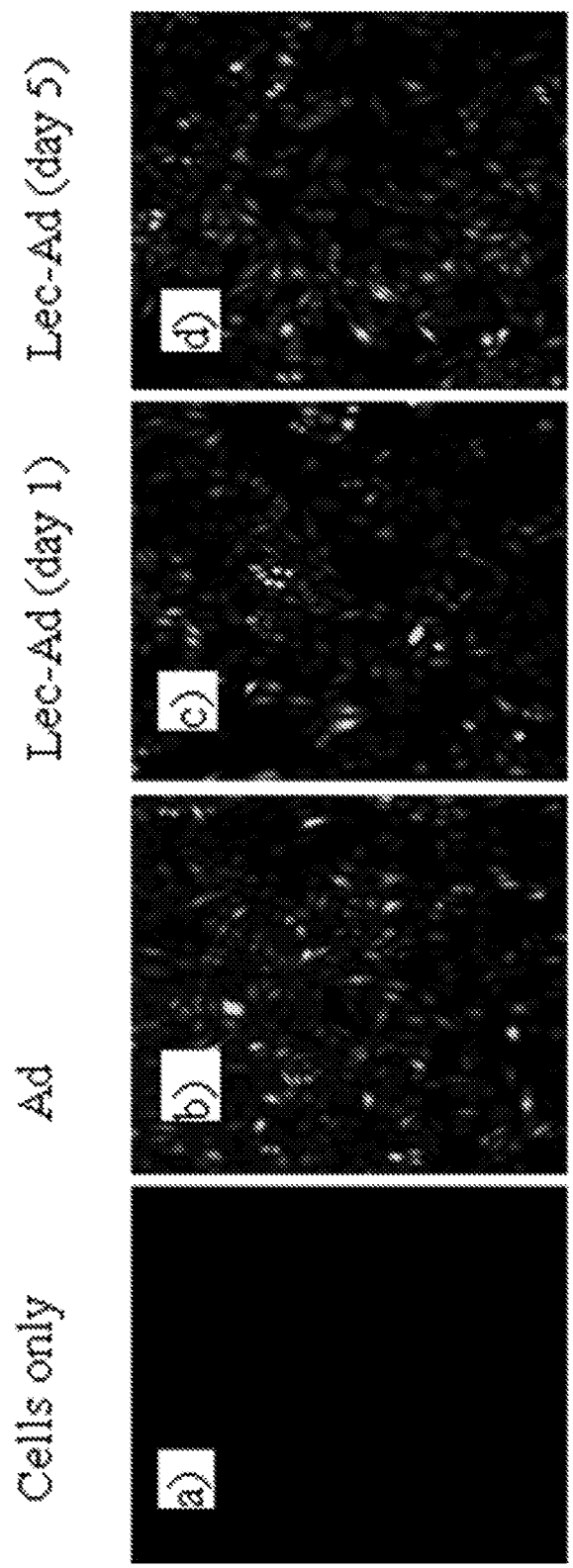
FIG. 10A-D illustrate the results of infecting HeLa cells with Ad-GFP which was encapsulated in lecithin liposomes using hydration process; wherein HeLa cells were plated 12 hours as shown in FIG. 10A, the cells were infected with Ad as shown in FIG. 10B, or Lecithin-Ad as shown in FIG. 10C, or Lecithin-Ad after the formulation was stored at 4° C. for 5 days and the experiment was repeated as shown in FIG. 10D.

The infectivity of the encapsulated virus was tested by infecting HeLa cells at a Multiplicity of Infectivity (MOI) of 4.3 plaque forming units per cell (pfu/cell). The mean fluorescence was measured using fluorescence microscopy as shown in FIG. 10.

When Ad is stored at 4° C. in PBS overnight, Ad loses transfection efficiency (data not shown). However, when Ad is encapsulated in Lecithin liposomes and stored at 4° C. for up to 5 days, Ad retains its' ability to infect cells as shown in FIG. 10d.

Example 13. Infectivity in HeLa Cells with Immunopurified Encapsulated Adenovirus In some embodiments of the instant invention, an immunoprecipitation (IP) technique based on anti-hexon IgG is used to precipitate free virus which was not encapsulated into the lecithin liposome. In this method, the lecithin-Ad liposome complexes were incubated with anti-hexon IgG after the encapsulation was completed. Hexon is a surface protein present on the adenovirus capsid necessary for internalization inside the cell therefore, anti-hexon was added to Ad or Lecithin-Ad samples and allowed to bind to non-encapsulated Ads in solution for 1 hour at 4° C. The samples were then incubated with magnetic Protein G beads suspended in 0.1M sodium biphosphate which has a high affinity for IgG. Non-encapsulated viruses were then extracted from the sample by applying a magnetic field. After the IP processing technique was employed, samples were added to cells, incubated for 24-48 hours and fixed using 2% PFA. Images were taken using a fluorescent microscope where green shows expression of recombinant GFP from the GFP-Ad vector used as shown in FIG. 3C.

As shown in FIG. 3C, transduction efficiency of Adenovirus in HeLa cells was not decreased when encapsulated in Lecithin liposomes.

Example 14. Infectivity in Lung Adenocarcinoma Cells

Figure 11:
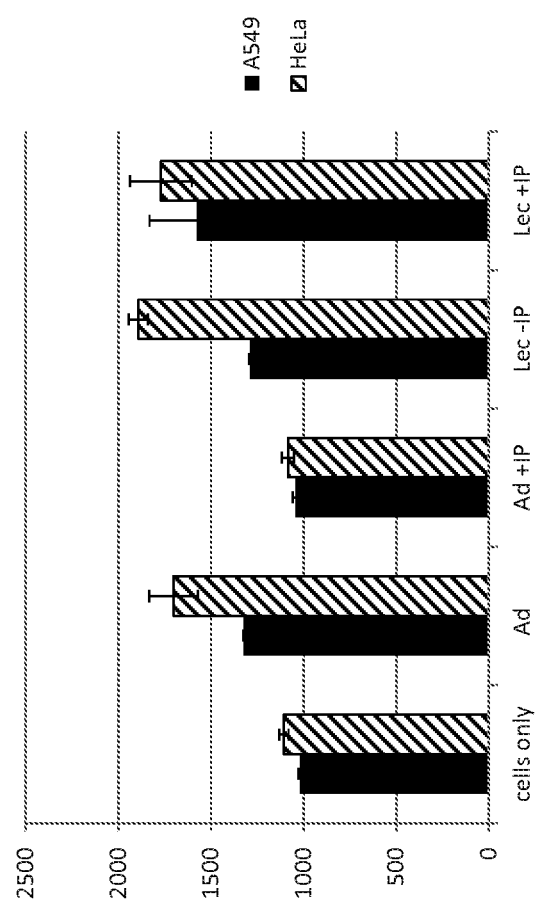
FIG. 11 illustrates transfection efficiency of Adenovirus (Ad) and Lecithin-Ad (Lec) before and after IP in A549 and HeLa cells.

Previous studies have shown that intranasal administration of Ad poorly penetrates alveolar epithelium by can be improved by the addition of pulmonary surfactant, a phospholipid-rich mixture (Balakireva et al. J. Virology, 2003). Therefore, lecithin liposomes were evaluated in human adenocarcinoma A549 lung cancer cells. The stimulation of Ad encapsulated in Lecithin liposomes showed an increase in transduction efficiency of compared to non-encapsulated Ad. Further, the uptake of 100 nm liposomes was enhanced after IP homogenization step. FIG. 11 shows the mean green fluorescence of GFP expression in HeLa cells (CAR++) and A549 cells (CAR+).

As shown in FIG. 11, HeLa cells readily uptake non-encapsulated Ad due to overexpression of the CAR receptor. Furthermore, HeLa cells also effectively uptake Lecithin-Ad liposome complexes. Conversely, CAR expression in A549 cells is not as abundant as in HeLa cells however, an uptake of Ad in A549 cells is enhanced when Ad is encapsulated in 100 nm lecithin liposomes. This allows for Adenovirus delivery to cells irrespective of CAR expression on the cell.

Example 15. Retention of Ad Encapsulation in Lecithin Liposomes

To test the retention of Ad encapsulated in lecithin liposomes, transfection of Ad in HeLa cells was analyzed. Lecithin liposomes were formulated and added to HeLa cells five days after formation. The green fluorescence expression was imaged as shown in FIG. 12.

Figure 12:
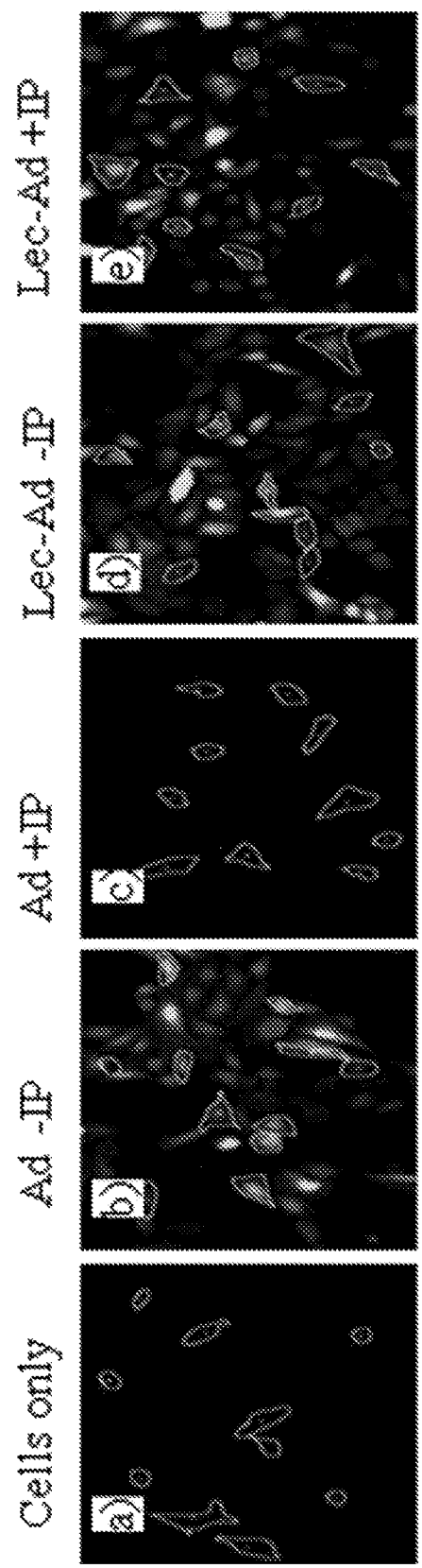
FIG. 12A-E illustrate infection experiments in HeLa cells in which cell outlines are made around cells using ImageJ software to calculate the mean green fluorescence for cell fluorescence analysis; wherein HeLa cells were plated at 30,000 cells/ml as shown in FIG. 12A and infected with non-encapsulated adenovirus as shown in FIG. 12B, or non-encapsulated adenovirus purified by immunoprecipitation as shown in FIG. 12C, or encapsulated adenovirus as shown in FIG. 12D, or encapsulated adenovirus which was further purified by immunoprecipitation FIG. 12E.
Figure 13:
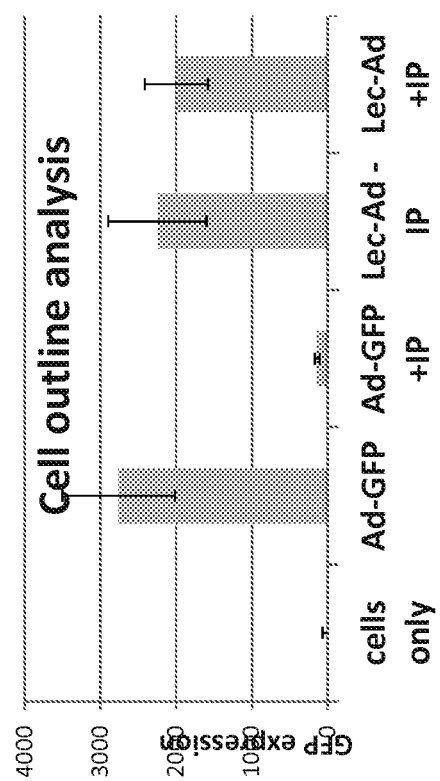
FIG. 13 illustrates ten HeLa cells were arbitrarily outlined using brightfield images, wherein an average mean green fluorescence for outlines is shown Avg FL±SD.

As shown in FIG. 12, the IP technique is an effective method to precipitate Ad in solution. The technique is fast (~2 hrs) and repeatable. Cell outline analysis allowed to analyze fluorescence without discriminating cell density variation from sample to sample. Ten cells were arbitrarily outlined and the mean fluorescence of the ten cells per sample were measured using Image J software as shown in FIG. 13.

When IP technique is applied to Lecithin liposomes, nearly 70% of Ads were shown to be encapsulated and retain viral infectivity after 5 days. Further, the technique has also indicated to have additional advantages such as homogenizing the sample size and decreasing the liposomes size due to the vigorous mixing of the liposome complexes with 2 μm nonporous magnetic beads. IP was performed on Lecithin-Ad liposomes and empty liposomes to test the infectivity of the virus after IP processing and the effect of size on the liposomes. IP was performed on three different batches on three separate days and the size and PDI was measured using DLS as shown in table 3.

TABLE 3

IP of encapsulated Adenovirus in Lecithin Liposomes

| Sample | Hydrodynamic Diameter (d · nm) | Polydispersity (PDI) |
|---|---|---|
| a) Adenovirus | 121 ± 1 | 0.03 |
| b) Lecithin-Ad liposome −IP | 360 ± 245 | 0.5 |
| c) Lecithin-Ad liposome +IP | 98 ± 12 | 0.3 |
| d) empty −IP | 738 ± 38 | 0.6 |
| e) empty +IP | 138 ± 3 | 0.4 |

Table 3 shows that the formation of lecithin-Ad liposomes after IP is stable (standard deviation of ±12 nm) compared to liposomes formed prior to IP with a large standard deviation in size. The polydispersity index is also reduced after IP signifying that the Lecithin-Ad liposomes are monodispersed (PDI≤0.3). Furthermore, this technique does not exhibit to decrease the number of encapsulated viruses in liposomes significantly or cause the virus to lose viral infective efficacy as seen in fluorescent images.

Example 16. Survival of Encapsulated Viruses

Figure 14:
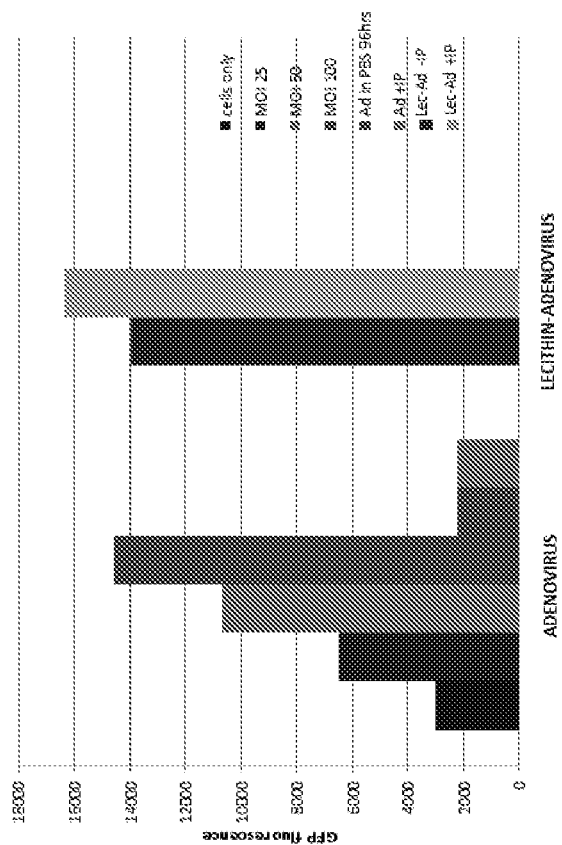
FIG. 14 illustrates stability and transfection efficiency of Ad vs. lecithin encapsulated Ad in Saline Buffer.

Survival of viruses and their ability to infect cells after encapsulation is an important factor necessary for its potential use as a therapeutic agent. When stored in saline buffer, Ad has shown to lose infectivity when kept in PBS for several days. Encapsulation of Ad in lecithin liposomes has shown that Ad retains viral infectivity in PBS even after four days. Therefore, stability of Adenovirus in saline buffer is improved while encapsulated as shown in FIG. 14. In this experiment, freshly thawed Ad was added to HeLa cells at MOI 0, 1.1, 2.2, or 4.3. A sample stored at 4° C. for 4 days was added before and after immunoprecipitation. Ad encapsulated in lecithin liposomes was added before and after IP stored in PBS after 4 days.

FIG. 14 shows that an increasing amount of infective adenovirus units added to cells (MOI 0-4.3) results with an increase of GFP expression. However, when Ad is stored in PBS for 4 days at 4° C. and added to cells at MOI 4.3, no GFP expression is detected suggesting that no infective units of Ad are present in solution. Conversely, when Ad-lecithin liposomes in PBS are added to cells at an MOI 4.3, a strong GFP expression is observed even after 4 days implying that Ad remains biologically active in PBS when encapsulated in lecithin liposomes.

Example 17. Efficacy of Systemic Delivery

An in vivo study in healthy immunocompetent mice is employed to investigate the blood circulation time of lecithin-adenovirus complexes compared to naked virus. Viral vectors are typically cleared from the bloodstream within 10 minutes which limits their effect as therapeutic agents. A study designed to compare persistence of Adenovirus (Ad) in blood of non-encapsulated (Ad) vs. encapsulated virus (Ad-liposome) at 5×10e9VP/mouse in healthy 8-week-old balb/c mice is assessed in order to determine if lecithin liposomes are effective carriers for systemic delivery.

Blood circulation time of Ad vs. Ad-liposome is tested within 30 min at time points t=0 (pre-injection), t=2 min, t=10 min, t=15 min, and t=30 min. Mice are anesthetized with isoflurane using precision vaporizer, and blood was collected at time points as stated above at a volume of 0.05-0.1 ml/draw via the submandibular vein bundle. Mice were euthanized after final blood draw by using CO2 followed by cervical displacement. Viral genome was detected using qPCR techniques. Maximum blood volume was collected from non-treated mice via cardiac puncture for PCR standard curve generation. Strain Balb/c mice Groups: 1) Ad5 (n=5), 2) Lecithin-Ad5 (n=5) 3) non-treated control (n=2)

Example 18. Effect of Immune Response after the Administration of Virus

An in vivo study in tumor-bearing 129/sv mice is used to test the effect of the innate and adaptive immune response after administration of encapsulated Adenovirus in lecithin liposomes. A cytokine release study is used to study the innate immune response within 72 hours. Cytokines will be detected using ELISA techniques. Neutralizing antibodies are measured to investigate the adaptive immune response before and after complete treatment. Serum neutralizing antibody titers are tested by adding serial dilutions to HeLa or A549 cells for their capacity to inhibit adenoviral vector infection. Neutralizing antibodies may be quantified by using an ELISA kit. Mice (n=5/group) receive iv injection of 1) TAV255, 2) TAV255-liposomes and 3) PBS (n=15 total) three times once a week. For biochemical analysis (CYTOKINES): Blood will be collected before first injection t=0, and after injection at t=12 h, t=36 hrs, and t=72 hrs at volumes of 0.05 ml for analysis of IL-6 and TNF using an ELISA kit. At endpoint (Day 60 or sooner if tumor size exceeds 1.5 cm): Euthanasia is performed by using CO2 followed by cervical displacement. Blood is collected. Strain: 129/sv mice Groups: 1) Ad (n=5), 2) Lecithin-Ad (n=5), 3) PBS (n=5)

Example 19. Anti-Tumoral Effects of TAV-255 In Vivo (IT and IV)

An in vivo investigation in tumor-bearing mice is utilized to test the anti-tumoral effects of encapsulated vs. non-encapsulated oncolytic virus after repeated systemic delivery.

The study is designed to determine the anti-tumoral effects of TAV-255 using lecithin liposomes as a carrier to subcutaneous tumor implants in an immunocompetent cancer mouse model. The anti-tumoral effects of bare adenoviral vectors to compare their efficacy are also evaluated. Treatment commences after a palpable tumor has developed in approximately 15-20 days post-subcutaneous tumor implantation. After the tumor is palpable, mice begin treatment. Mice receive IT or IV injection of 1) TAV-255, 2) TAV-255-liposomes and 3) PBS, every three days and tumor growth and condition of mouse health (coat, behavior, weight) is monitored. Mice are euthanized at endpoint (Day 60 or sooner if tumor size exceeds 1.5 cm) by CO2 and cervical dislocation. Virus titers are quantified from tumor biopsies utilizing a standard virus plaque assay with HEK293 cells. Also, paraffin-embedded tumor sections are analyzed for virus infection by immuno-fluorescence microscopy utilizing an anti-hexon antibody (EMD Millipore Inc.). After mice are sacrificed and tumors are harvested, a full evaluation of tumor histology is carried out.

The amount of apoptotic activity is evaluated using TUNEL Apoptosis Detection Kit (EMD Millipore) and separately utilizing an antibody against active-caspase 3 protein. The degree of virus-mediated histopathology and immune infiltration is determined and quantified in tumor sections using antibodies against T cells, B cells, and macrophages. Quantification of fluorescent images are carried out by ImageJ analysis. Also, the number of proliferating cells in tumor sections is quantified by Ki67 staining.

Example 20. Adaptive Immune Response after Administration

An in vivo study to monitor neutralizing antibody titers during TAV-255 treatment will be utilized to assess how encapsulated viruses impact the amount of circulating neutralizing antibodies. 0.05 ml of blood is collected in EDTA vacutainers from 129/sv mice undergoing TAV-255 treatment (it or iv) via the submandibular vein bundle. Blood is centrifuged and plasma is collected. A neutralization assay is used to assess the antibody titer or naked Ad vs. encapsulated virus.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

exposing it to a physiological solution, and thereby forming multilamellar vesicles;
d) sonicating said vesicles and thereby forming a formulation with recombinant adenovirus particles encapsulated in the anionic liposomes;
e) binding non-encapsulated recombinant adenovirus particles with an antibody; and
f) separating the encapsulated recombinant adenovirus particles from the non-encapsulated recombinant adenovirus particles bound to the antibody by magnetic immunoprecipitation with magnetic beads linked to protein G; and thereby extracting the non-encapsulated recombinant adenovirus particles from the formulation.

2. The method of claim 1, wherein the organic solvent is chloroform.

3. The method of claim 1, wherein the binding is conducted with anti-hexon IgG, anti-penton IgG or anti-fiber IgG.

4. The method of claim 1, wherein the adenovirus is Ad5.

5. The method of claim 1, wherein a PEG-folate complex is further added to the mixture of step a).

6. A formulation comprising a recombinant adenoviral particle encapsulated in an anionic liposome, wherein the formulation is obtained by the method of claim 1.

7. A method of treating a cancer patient, the method comprising administering to the cancer patient a formulation prepared by the method of claim 1, the formulation comprising a recombinant Ad5 adenoviral particle encapsulated in an anionic liposome comprising lecithin, cholesterol, PEG, and a folate moiety, said formulation being purified

What is claimed is:

1. A method of preparing a formulation comprising a viral particle encapsulated in an anionic liposome, wherein the viral particle is a recombinant adenovirus, the method comprising:
   a) preparing a mixture by dissolving lecithin, cholesterol and PEG in an organic solvent;
   b) drying the mixture under vacuum to form a dry lipid film;
   c) mixing the dried lipid film with recombinant adenovirus particles and hydrating the dried lipid film by from non-encapsulated recombinant Ad5 adenoviral particles by binding of the non-encapsulated recombinant Ad5 adenoviral particles with an antibody and immunoprecipitating the non-encapsulated recombinant Ad5 adenoviral particles bound to the antibody with magnetic beads linked to protein G.

8. The method of claim 7, wherein the patient is a metastatic cancer patient.

9. The method of claim 7, wherein the patient is afflicted with a cancer selected from the group consisting of lung cancer, cervical cancer and breast cancer.

10. The method of claim 7, wherein the patient is a cancer patient, and wherein the cancer is an epithelial cancer.

11. The method of claim 7, wherein the patient is a cancer patient whose cancer cells express a folate receptor.

\* \* \* \* \*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Primer for construction of adenovirus

<400> SEQUENCE: 1
tggctgttaa aggcagtttg g                                             21

<210> SEQ ID NO 2
<211> LENGTH: 23
<212> TYPE: DNA
<213> ORGANISM: Artificial Sequence
<220> FEATURE:
<223> OTHER INFORMATION: Primer for construction of adenovirus

<400> SEQUENCE: 2
gcactccatt ttcgtcaaat ctt                                           23
```